(12) United States Patent
Li et al.

(10) Patent No.: US 10,947,267 B2
(45) Date of Patent: Mar. 16, 2021

(54) SYSTEM AND METHOD FOR SOLUTION PHASE GAP PEPTIDE SYNTHESIS

(71) Applicant: Texas Tech University System, Lubbock, TX (US)

(72) Inventors: Guigen Li, Lubbock, TX (US); Cole Seifert, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/739,391

(22) PCT Filed: Dec. 21, 2016

(86) PCT No.: PCT/US2016/068112
§ 371 (c)(1),
(2) Date: Dec. 22, 2017

(87) PCT Pub. No.: WO2017/112809
PCT Pub. Date: Jun. 29, 2017

(65) Prior Publication Data
US 2019/0330262 A1 Oct. 31, 2019

Related U.S. Application Data

(60) Provisional application No. 62/270,432, filed on Dec. 21, 2015.

(51) Int. Cl.
*C07K 1/06* (2006.01)
*C07F 9/53* (2006.01)

(52) U.S. Cl.
CPC ............ *C07K 1/061* (2013.01); *C07F 9/5325* (2013.01)

(58) Field of Classification Search
CPC .............................. C07K 1/061; C07F 9/5325
See application file for complete search history.

(56) References Cited

U.S. PATENT DOCUMENTS

| | | | |
|---|---|---|---|
| 5,516,891 | A | 5/1996 | Siwruk et al. |
| 6,753,409 | B1 | 6/2004 | Chrzan et al. |
| 8,383,770 | B2 | 2/2013 | Dalton et al. |
| 8,716,439 | B2 | 5/2014 | Murao et al. |
| 9,353,148 | B2 | 5/2016 | Takahashi |
| 2001/0018512 | A1 | 8/2001 | Blanchard |
| 2008/0287649 | A1 | 11/2008 | Chen et al. |
| 2014/0100355 | A1 | 4/2014 | Acemoglu et al. |
| 2014/0178302 | A1 | 6/2014 | Lattuada et al. |
| 2014/0213814 | A1 | 7/2014 | Monnaie et al. |
| 2016/0257725 | A1 | 9/2016 | Verdine et al. |
| 2018/0215782 | A1 | 8/2018 | Kono et al. |

FOREIGN PATENT DOCUMENTS

| | | | |
|---|---|---|---|
| EP | 2716650 | A1 | 4/2014 |
| WO | 93/25571 | A1 | 12/1993 |
| WO | 2011152603 | A1 | 12/2011 |
| WO | 2013/117440 | A1 | 8/2013 |
| WO | 2017/112809 | A1 | 6/2017 |

OTHER PUBLICATIONS

Chemical Abstract Service STN Database, Registry No. 5068-20-2 [Entered STN: Nov. 16, 1984]. (Year: 1984).*
Chemical Abstract Service STN Database, Registry No. 2272-04-0 [Entered STN: Nov. 16, 1984]. (Year: 1984).*
Seifert et al. Eur. J. Org. Chem. 2016, 1714-1719. (Year: 2016).*
Ai, T. et al. "Chiral N-phosphonyl imine chemistry: Asymmetric synthesis of α, ⊕-diamino esters by reacting phosphonyl imines with glycine enolates." Bioorg. Med. Chem. Lett. 2009, 19, 3967-3969.
Amblard, M. et al. "The Fundamentals of Fmoc Solid-Phase Peptide Synthesis." Idenshi Igaku Ivfook 2012, 21, 36-42.
Behrendt, R. et al. "New t-butyl based aspartate protecting groups preventing aspartimide formation in Fmoc SPPS." Journal of Peptide Science 2015, 21, 680-687.
Brieke, C. et al. "A Facile Fmoc Solid Phase Synthesis Strategy to Access Epimerization-Prone Biosynthetic Intermediates of Glycopeptide Antibiotics." Organic Letters 2014, 16, 2454-2457.
Chandrudu, S. et al. "Chemical Methods for Peptide and Protein Production." Molecules 2013, 18, 43 73.
Chen, C.-C. et al. "A mild removal of Fmoc group using sodium azide." Amino Acids 2014, 46, 367-374.
Dailler, D. et al. "A General and Scalable Synthesis of Aeruginosin Marine Natural Products Based on Two Strategic C (sp(3))-H Activation Reactions." Angell'andte Chemie-International Edition 2015, 54, 4919-4922.
Fu, T. T. et al. "Palladium-catalyzed air-based oxidative coupling of arylboronic acids with H-phosphine oxides leading to aryl phosphine oxides." Organic & Biomolecular Chemistry Feb. 26, 2014, 12, 2895-2902.
Han, J. et al. "Chiral N-phosphonyl imine chemistry: asymmetric additions of ester enolates for the synthesis of β3-amino acids." Chem. Biol. Drug Des. 2008, 72, 120-126.
Isidro-Llobet, A. et al. "Amino Acid-Protecting Groups." Chem. Rev. 2009, 109, 2455-2504.
Janssen et al. Click Dendritic Phosphines: Design, Synthesis, Application in Suzuki Coupling, and Recycling by Nanofiltration, Advanced Synthesis & Catalysis, Feb. 9, 2009 (Feb. 9, 2009), vol. 351, p. 313-318; p. 314.
Kattamuri, P. V. et al. "Asymmetric Synthesis of a-Amino-1,3-dithianes via Chiral N-Phosphonyl Imine-Based Umpolung Reaction Without Using Chromatography and Recrystallization." J. Org. Chem. 2011, 76, 2792-2797.

(Continued)

*Primary Examiner* — Amanda L. Aguirre
(74) *Attorney, Agent, or Firm* — Edwin S. Flores; Daniel J. Chalker; Chalker Flores, LLP

(57) ABSTRACT

Disclosed is a system and method for Fmoc/tBu solution-phase peptide synthesis including the development of a new benzyl-type GAP protecting group, and related uses thereto. This novel GAP protecting group is utilized in place of a polymer support, facilitating C to N Fmoc peptide synthesis without chromatography, recrystallization, or polymer supports. The GAP group can be added and removed in high yield.

9 Claims, 13 Drawing Sheets

(56) References Cited

OTHER PUBLICATIONS

Kattuboina, A. et al. "Chiral N-phosphonyl imine chemistry: asymmetric 1,2-additions of allylmagnesium bromides." Tetrahedron Lett. 2008, 49, 3722-3724.
Kattuboina, A. et al. "Chiral N-phosphonyl imine chemistry: new reagents and their applications for asymmetric reactions." Tetrahedron Lett. 2008, 49, 1573-1577.
Kaufmann, E. et al. "Total Synthesis of the Glycosylated Macrolide Antibiotic Fidaxomicin." Organic Letters 2015, 17, 3514-3517.
Mochizuki, M. et al. "Regioselective Formation of Multiple Disulfide Bonds with the Aid of Postsynthetic S-Tritylation." Organic Letters 2015, 17, 2202-2205.
Mollica, A. et al. "The Evolution of Peptide Synthesis: From Early Days to Small Molecular Machines." Curr. Bioact. Compd. 2013, 9, 184-202.
Pindi, S.; Kaur, P.; Shakya, G.; Li, G. N-Phosphinyl Imine Chemistry (1): Design and Synthesis of Novel N-Phosphinyl Imines and their Application to Asymmetric aza-Henry Reaction. Chem. Biol. Drug. Des. 2011, 77, 20-29.
Pubmed Compound Summary for CID 71676245, 'AKOS016034578', U.S. National Library of Medicine, Sep. 4, 2013 (Sep. 4, 2013), p. 3 (https://pubchem.ncbi.nlm.nih.gov/compound/71676245#section= Top).
Sharma, P. K. et al. "Total Synthesis of Proanthocyanidin A1, A2, and Their Stereoisomers." 0rganic Letters 2015, 17, 2306-2309.
Shelton, P. T. et al. "Linkers, Resins, and General Procedures for Solid-Phase Peptide Synthesis." In Peptide Synthesis and Applications, 2nd Edition, Jensen, K J.; Shelton, P. T.; Pedersen, S. L., Eds. Humana Press Inc: Totowa, 2013; vol. 1047, pp. 23-41.
Shi, JVL et al. "Determination of thymopentin in beagle dog blood by liquid chromatography with tandem mass spectrometry and its application to a preclinical pharmacokinetic study." Journal of Separation Science 2015,38, 1351-1357.
Spinella, M. et al. "The dimethylsulfoxonium methylide as unique reagent for the simultaneous deprotection of amino and carboxyl function of N-Fmoc-a-amino acid and N-Fmoc-peptide esters." Tetrahedron 2013, 69, 2010-2016.

Wu, J. et al. "Solution phase-peptide synthesis via the group-assisted purification (GAP) chemistry without using chromatography and recrystallization." Chem. Commun. 2014, 50, 1259-1261.
Xie et al. "Group-assisted purification (GAP) chemistry for the synthesis of Velcade via—asymmetric borylation of N-phosphinylimines" Beilstein Journal of Organic Chemistry, Mar. 31, 2014 (Mar. 31, 2014), vol. 10, p. 746-751.
Zhu, M.-X. et al. "Thymopentin enhances the generation of T-cell lineage derived from human embryonic stem cells in vitro." Experimental Cell Research 2015, 331, 387-398.
International Search Report and Written Opinion—PCT/US2016/068112 dated May 8, 2017.
Registry RN 1215304-35-0 Apr. 1, 2010.
Extended European Search Report (EP 16880050.6) dated Aug. 27, 2019.
De Marco et al. "C_, N And N _, C Solution Phase Peptide Synthesis Using the N-acyl 4-Nitrobenzenesulfonamide as Protection of the Carboxylic Function," Organic & Biomolecular Chemistry, Jul. 21, 2013 (Jul. 21, 2013), vol. 11, Iss. 23, pp. 3786-96.
Hou et al. "Progress in Chemical Synthesis of Peptides and Proteins," Transactions of Tianjin University, Jun. 23, 2017 (Jun. 23, 2017), vol. 23, Iss. 5, pp. 401-419.
Lawrenson et al. "The Greening of Peptide Synthesis," Green Chemistry, Mar. 2, 2017 (Mar. 2, 2017), vol. 19, No. 1, pp. 1685-1691.
Seifert et al. "GAP Peptide Synthesis via Design of New GAP Protecting Group: An Fmoc/tBu Synthesis of Thymopentin Free from Polymers, Chromatography and Recrystallization,"European Journal of Organic Chemistry, Mar. 8, 2016 (Mar. 8, 2016), vol. 2016, Iss. 9, pp. 1714-1719.
Pubchem. CID 129303937. Aug. 4, 2017, pp. 1-11. Retrieved from the Internet <URL: https://pubchem.ncbi.nlm.nih.gov/compound/129303937>; p. 2, formula.
International Search Report, PCT/US2019/029569 dated Jul. 12, 2019.
International Search Report, PCT/US2019/033296 dated Jul. 15, 2019.
International Search Report, PCT/US2020/015132 dated Jun. 4, 2020.

* cited by examiner

SYSTEM AND METHOD FOR SOLUTION PHASE GAP PEPTIDE SYNTHESIS

CROSS-REFERENCE TO RELATED APPLICATIONS

This application claims priority to and is a U.S. National Stage Patent Application of International Application No. PCT/US2016/068112, filed Dec. 21, 2016, which claims priority to U.S. Patent Appl. Ser. No. 62/270,432, filed Dec. 21, 2015, entitled "System And Method For Solution Phase GAP Peptide Synthesis." The foregoing patent applications are hereby incorporated by reference herein in their entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present disclosure relates in general to the field of peptide synthesis. In particular, the system provides for solution-phase peptide synthesis without chromatography, recrystallization, or polymer supports, and allows for high overall yield and purity. The disclosed systems and methods support a wide variety of scenarios and include various products and services.

STATEMENT OF FEDERALLY FUNDED RESEARCH

None.

BACKGROUND OF THE DISCLOSURE

Recent research efforts have made significant advancements in the area of purification chemistry, focusing specifically on avoiding column chromatography and recrystallization. This research has been defined as Group-Assisted Purification (GAP) chemistry/technology as a chemistry for organic synthesis that avoids traditional purification methods such as chromatography and/or recrystallization by purposefully introducing a well-functionalized group in the starting material or in the newly generated product. Such research has the potential to encompass the entire field of synthetic organic chemistry.

One area where protecting groups are used extensively is in peptide synthesis, both for solid and solution phase approaches. Developed by Merrifield in the 1960's, Solid-Phase Peptide Synthesis (SPPS) has become a standard protocol used by multiple scientific disciplines for research and manufacturing (See FIG. 1A). The advantages of the polymer support lie in its ability to allow facile purification of the growing peptide after each coupling/deprotection step, which avoids the use of column chromatography. The key disadvantage of SPPS lies in the difficulty of scale-up: many polymer supports are expensive, and occupy the vast majority of the mass of the material to be worked with. Protecting groups are found in almost every complex synthesis where multiple functional groups are present. Effective protecting groups need to be robust to a wide variety of conditions, and must be added and removed with high yield. An ideal example for GAP chemistry would be one in which a semi-permanent protecting group introduced the necessary solubility characteristics required for GAP. However, most traditional protecting groups are nonpolar, and therefore do not generate the required GAP solubility for most substrates. If a protecting group could be developed that generated adequate solubility control, then GAP chemistry could potentially be extended to all syntheses, which require the use of that protecting group.

Several approaches have been utilized. Published patent application WO 2014093723 A2, teaches the protection of imines with a GAP-equipped chiral auxiliary, then using these chiral, N-phosphonyl imines as electrophiles in asymmetric boron addition reactions. Purification was conducted via GAP processes. This work is valuable in that it provides facile access to chiral, α-boronic acid amines, which could potentially be used to synthesize novel amino acid derivatives, which could potentially be incorporated into novel peptide targets.

U.S. Pat. No. 8,383,770 B2 teaches the use of the Fmoc and Boc N-terminus protecting groups in SPPS. This technology is well known and widely applied in industry. Boc and Fmoc groups have been used for decades in all areas of peptide chemistry, and the preferred Fmoc group is almost entirely restricted to solid phase. Examples of economically feasible Fmoc protection schemes in solution are non-existent, with few examples in the literature at all.

U.S. Pat. No. 5,516,891 A provides one of the few examples of Fmoc-based SolPPS. Again, the Fmoc peptide synthesis is almost entirely restricted to SPPS, due to the formation of N-fluorenylmethylpiperidine (NFMP) as a side product during deprotection, which is difficult to remove without polymer supports. The standard protocol for Fmoc deprotection is to stir the Fmoc-peptide in a solution of DMF or DCM with excess piperidine, deprotecting the Fmoc group and forming NFMP in the process. The '891 patent teaches removal of this impurity by deprotecting with 4-aminomethylpiperidine (4AMP) instead of piperidine. This forms NFMP-CH2NH2 instead of NFMP, which due to the presence of the extra amino group, can be extracted into water. The problem with this method lies in the high cost of using 4AMP. Per Sigma Aldrich, 4AMP costs $3.80 per gram, while piperidine only costs $0.12 per gram. This is why this method is cost prohibitive, and why it has not been accepted by the industry.

It is therefore a need in the art to develop an economically feasible GAP peptide synthesis system capable of overcoming these limitations, while keeping the purification benefits of solid phase peptide synthesis.

SUMMARY OF THE DISCLOSURE

The present disclosure addresses failings in the art by providing a system and method for peptide synthesis utilizing a reaction which occurs in solution phase, without the mass waste of polymer supports, but retains all of the purification benefits of SPPS as an alternative to both traditional solution-phase peptide synthesis (SolPPS) as well as SPPS, affording advantages of both methods. By utilizing the advantages of GAP chemistry, an Fmoc-SolPPS strategy is presented that is economically feasible and useful for the commercial production of peptides.

It is therefore an object of the present disclosure to enable GAP peptide synthesis (GAP-PS) via the development of a new GAP benzyl-type protecting group for C-terminus protection (See FIG. 1B). In connection with C-terminus protection, GAP-PS may be achieved using an Fmoc/tBu strategy, which is the most used method in SPPS due to its mild deprotection protocols. This strategy is currently almost entirely restricted to SPPS due to the formation of N-fluorenylmethylpiperidine (NFMP) as a side product during deprotection, which is difficult to remove without polymer supports. It is therefore an object of the present disclosure to provide over 1 gram of target peptide, such as thymopentin, in high yield and high purity via utilization of a solution-phase Fmoc/tBu strategy as an example for a general method of peptide synthesis. Protection of various amino acids with this new protecting group has also been achieved in consistent quantitative yield.

In one aspect, a method for peptide synthesis is provided. The method allows for a high yield (over 50%) with high purity (99%) using the Fmoc/tBut strategy with solution-phase peptide synthesis (SolPPS). The present invention utilizes Group-Assisted Purification (GAP) in conjunction with SolPPS, enabling the peptide to be purified through precipitation instead of recrystallization or chromatography. The disclosed method also avoids solid-phase peptide synthesis (SPPS), thereby increasing the amount of product that is actually formed It is another object of the present invention to provide a novel C-terminus protecting group (referred to herein as "BnDppOH", "BnDppYH", "BzDppOH") which is chemically linked to the C-terminus. The use of this GAP group is also different: whereas previous GAP groups served as amino protecting groups, the present invention discloses a protecting group for the carboxylic acid. By protecting the carboxylic acid, peptide synthesis is allowed in an industry-preferred C to N direction rather than the N to C direction, a critical difference from previous GAP-PS methods, further enabling the use of Fmoc as a temporary protecting group with which to grow the peptide chain. During Fmoc deprotection, NFMP is formed which is difficult to remove without solid supports. The present invention provides a method of removal to selectively precipitate the GAP-peptide, thereby leaving NFNIP in solution.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION OF THE DISCLOSURE

Figure 1A:
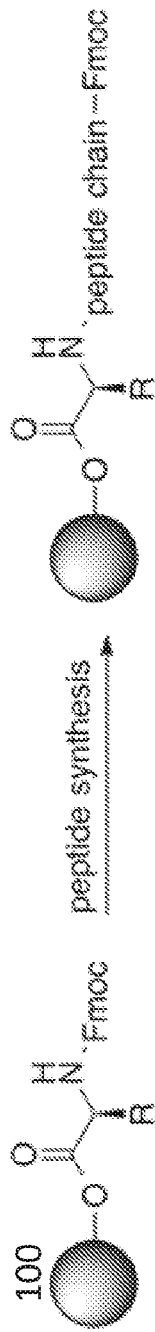
FIG. 1A depicts a prior art process of Solid Phase Peptide Synthesis (SPPS).
Figure 1B:
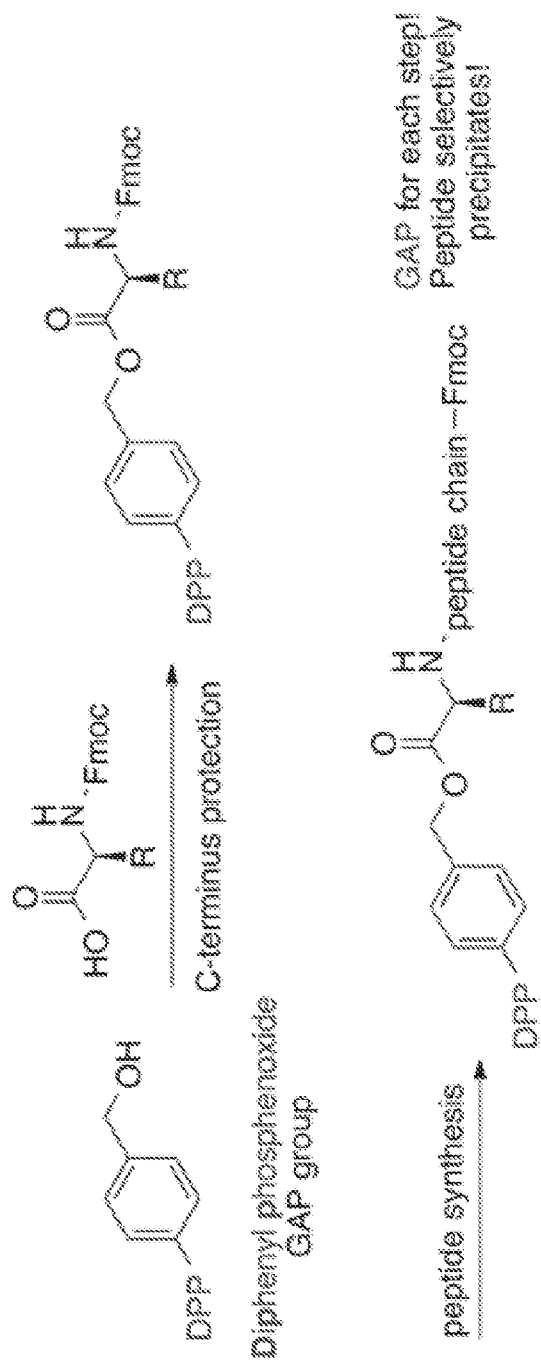
FIG. 1B depicts a process of the present disclosure including the use of a benzyl-type protecting group for C-terminus protection.

While the making and using of various embodiments of the present disclosure are discussed in detail below, it should be appreciated that the present disclosure provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present disclosure will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, compositions, or systems. Accordingly, embodiments may, for example, take the form of methods, compositions, compounds, materials, or any combination thereof. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

It is therefore an embodiment of the present disclosure to provide a system and method for a new C-terminus protecting group. In designing the new protecting group, it was apparent that the GAP-functionalized segment of the protecting group would need to be stable to a wide variety of conditions. Considerations were taken that it must provide the necessary solubility characteristics for GAP chemistry. Also, it must work efficiently and orthogonally with the reactivity of current protection strategies. A modified benzyl protecting group was thus utilized in order to keep the desirable reactivity while introducing the GAP group. The GAP group chosen is diphenylphosphine oxide, due to known previous success with phosphine oxide groups using GAP chemistry. Also, attachment of this group onto the para position of the benzyl group creates a triphenylphosphine oxide moiety, which is widely known in the literature to be stable to an extensive variety of conditions. This stability is necessary to avoid interference with the multiple deprotection conditions that the substrate may be exposed to, thereby establishing true orthogonality.

Initial efforts focused on the development of chiral, N-phosphonyl and N-phosphinyl imine chemistry for the synthesis of chiral amines, with much success. By controlling solubility, the chiral amine products can be selectively precipitated from the crude mixture, thereby avoiding chromatography and recrystallization. Further efforts have extended this technology to other substrates and functional groups. In order to do this, the GAP properties are taken from chiral auxiliaries and, with modification, present the basis for the GAP protecting groups of the present disclosure.

Figure 2:
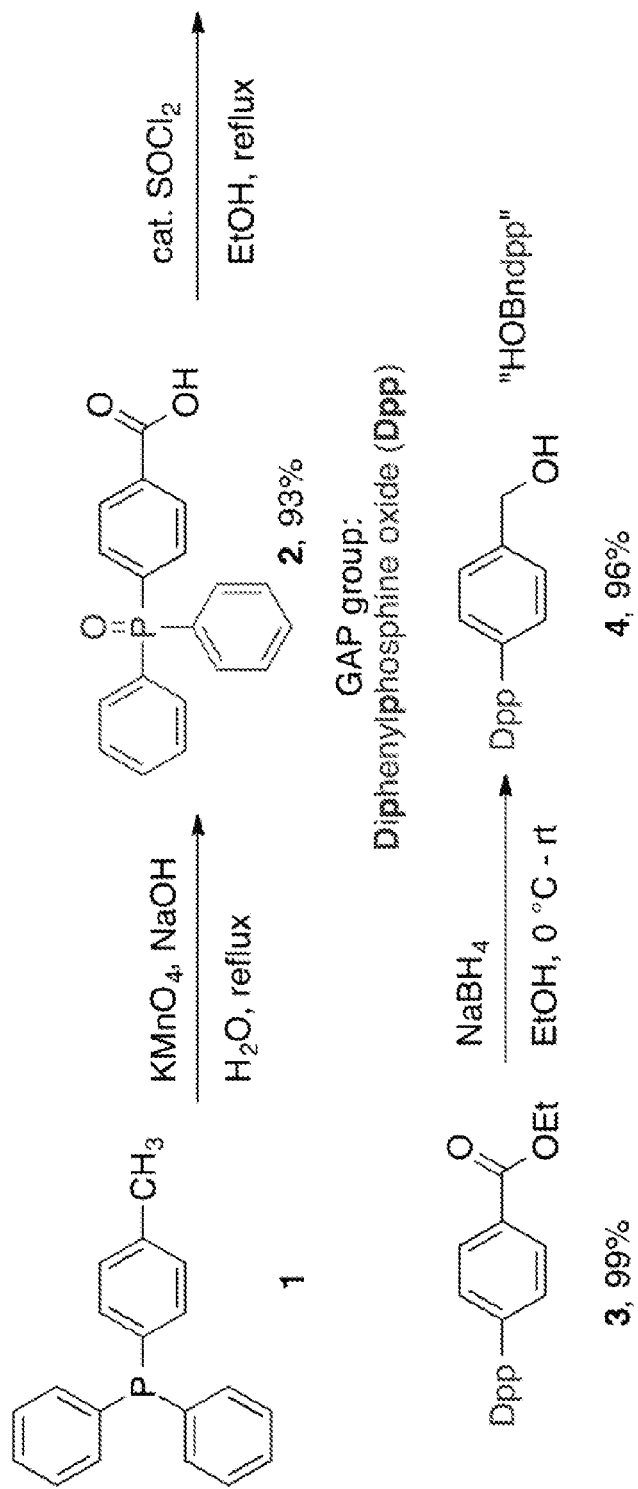
FIG. 2 depicts a process for development of a protecting group utilized in FIG. 1B.
Figure 3:
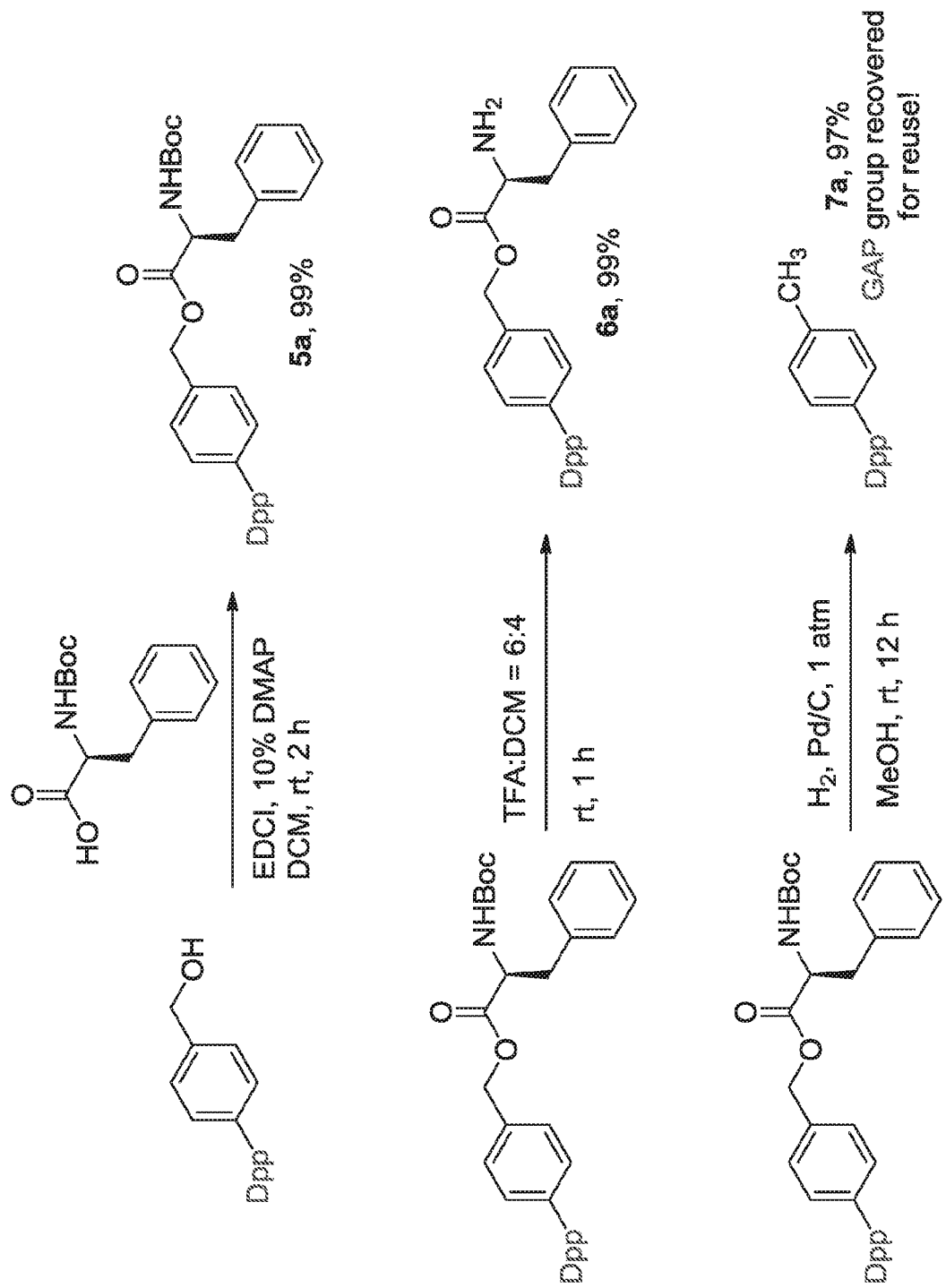
FIG. 3 depicts a schematic for testing the orthogonality and GAP capability of the protecting group of FIG. 2.

In an exemplary embodiment of the present disclosure, synthesis of this new protecting group begins with commercially available, diphenyl(p-tolyl)phosphine 1 (FIG. 2). Oxidation of 1 with potassium permanganate provides benzoic acid 2, as well as the GAP group through phosphine oxidation. This GAP group is diphenylphosphine oxide (Dpp). Esterification followed by borohydride reduction affords the GAP-equipped benzyl alcohol 4, or "BndppOH" (alternatively "HOBndpp"), in high yield. Next, the orthogonality and the GAP capabilities of this new protecting group are tested. Protection of Boc-Phe-OH was both facile and quantitative using EDCI as the carbodiimide coupling reagent (FIG. 3). The product 5a can be selectively precipitated from an ethyl acetate/petroleum ether solvent mixture as a white solid, thereby satisfying the requirements of GAP chemistry. Deprotection of the Boc group was also quantitative, and did not result in any loss of the Bndpp group. The Bndpp group can be easily removed using catalytic hydrogenation, and also can be recovered and recycled as "HBndpp" 7a for reuse after washing away the deprotected amino acid. Subjection of 7a to permanganate oxidation affords 2, which can be transformed into HOBndpp 4 as previously mentioned (FIG. 2).

Figure 4A:
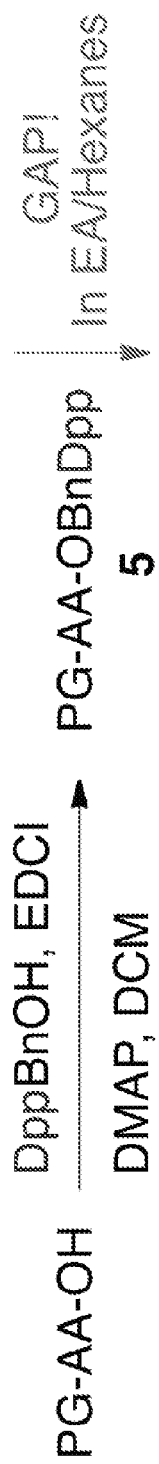
FIGS. 4A-4B each depicts a schematic for the process of attaching the protecting group of FIG. 2 to various amino acids.
Figure 4B:
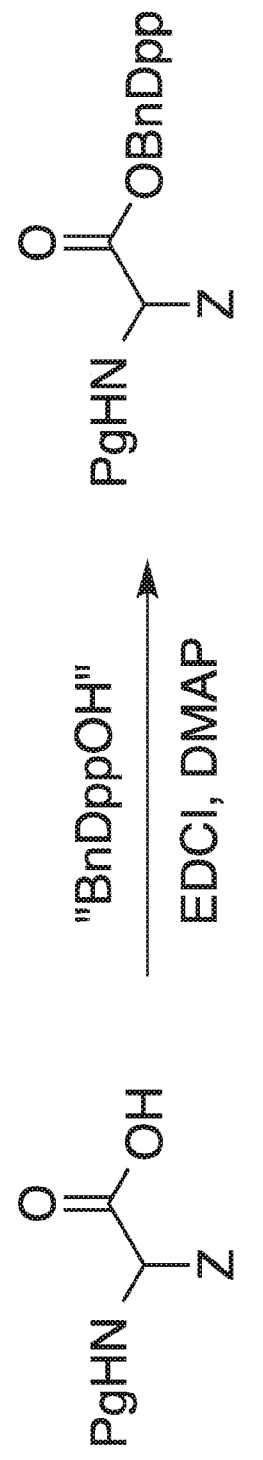

FIGS. 4A-4B depict a schematic for the process of attaching the protecting group of FIG. 2 to various amino acids. A full substrate scope for amino acid protection is shown below in TABLE 1, with consistent quantitative yields for the protection of a variety of Boc and Fmoc amino acids with varying side-chain protecting groups. Of note is the quantitative protection of tryptophan, arginine, valine, and cysteine.

TABLE 1

| Product | PG- | -AA- | Yield |
|---------|------|-----------|-------|
| 5a | Boc- | -Phe- | 99% |
| 5b | Boc- | -Cys(Acm)- | 99% |
| 5c | Fmoc- | -Lys(Boc)- | 99% |
| 5d | Fmoc- | -Asp(tBu)- | 99% |
| 5e | Fmoc- | -Trp(Boc)- | 97% |
| 5f | Fmoc- | -Arg(Pbf)- | 99% |
| 5g | Fmoc- | -Val- | 99% |
| 5h | Fmoc- | -Asn(Trt)- | 99% |
| 5i | Fmoc- | -Ala- | 99% |
| 5j | Fmoc- | -Gly- | 99% |
| 5k | Fmoc- | -Tyr(tBu)- | 99% |

In one embodiment a method for Fmoc/tBu liquid-phase peptide synthesis via GAP chemistry/technology is presented, along with the development of a new benzyl-type GAP protecting group for carboxylic acids. This new GAP protecting group is utilized in place of a polymer support, and facilitates C to N Fmoc peptide synthesis without chromatography or recrystallization. The GAP protecting group can be added and removed in high yield, while maintaining an orthogonal relationship to the other protecting groups present. As a first test of this new protecting group for GAP peptide synthesis, over 1 gram of the pentapeptide drug thymopentin (an immunostimulant) was synthesized in high overall yield (83%) and high purity (99%).

In one embodiment of the present invention, a protecting group is presented for Group Assisted Purification (GAP) peptide synthesis, comprising the following compounds:

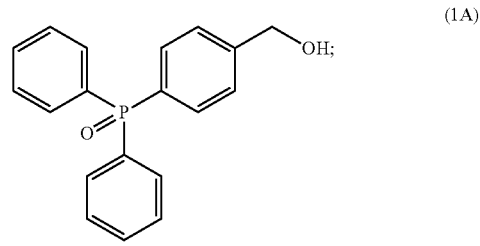 [SMILES: O=P(c1ccccc1)(c1ccccc1)c1ccc(CO)cc1]

(1A)

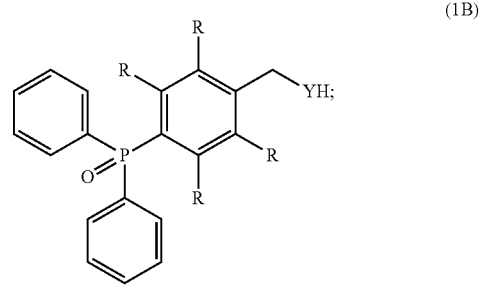

(1B)

-continued (1C)
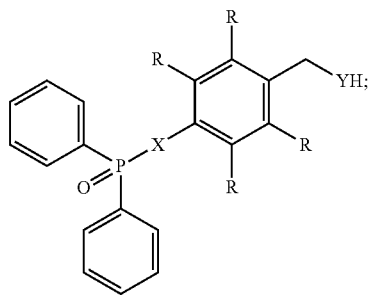

(1D)
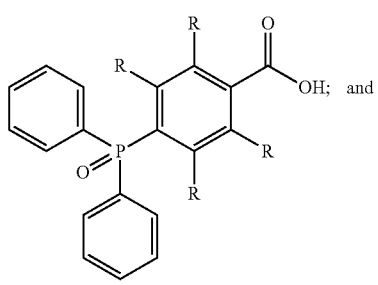
OH; and (1E)
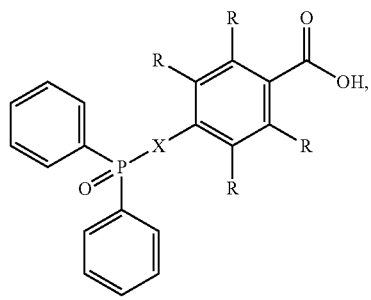
OH, wherein: R is: H, Me, or OMe; Y is: O, S, and NH; and X is: O, S, or NH.

In another embodiment, the present invention provides a method of forming a protecting group for C-terminus protection, comprising of Fmoc-tBu-based solution phase peptide synthesis (SolPPS). The method includes protecting group:

(1A)
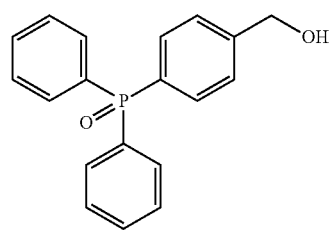

which is produced by the following:

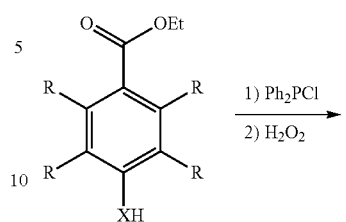

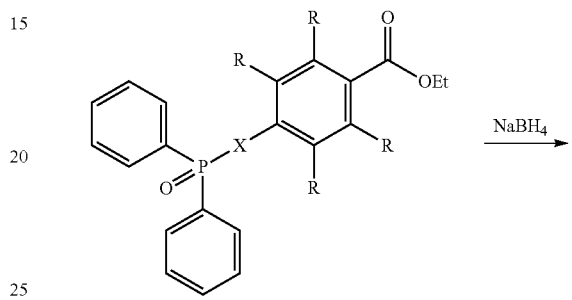

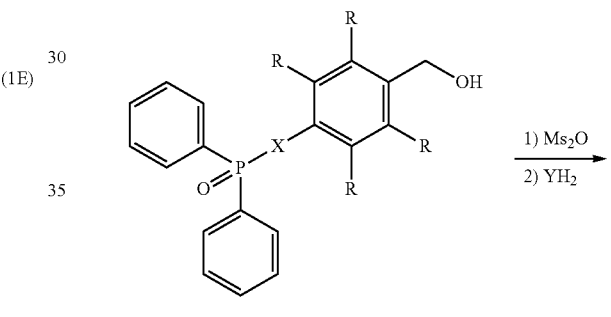

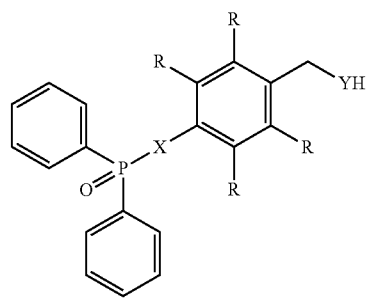

R = H, Me, OMe
X = O, S, NH
Y = O, S, NH wherein, said protecting group IS formed by refluxing (p-tolyl)diphenylphosphine with potassium permanganate (KMnO4), isolating the carboxylic acid product, refluxing the carboxylic acid product in acidic ethanol (EtOH, H+), and adding sodium borohydride (NaBH4).

In another embodiment, the present invention presents a method of producing protecting group:

9

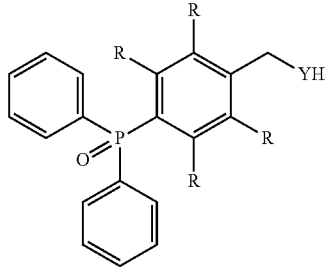

(1B)

produced by the following:

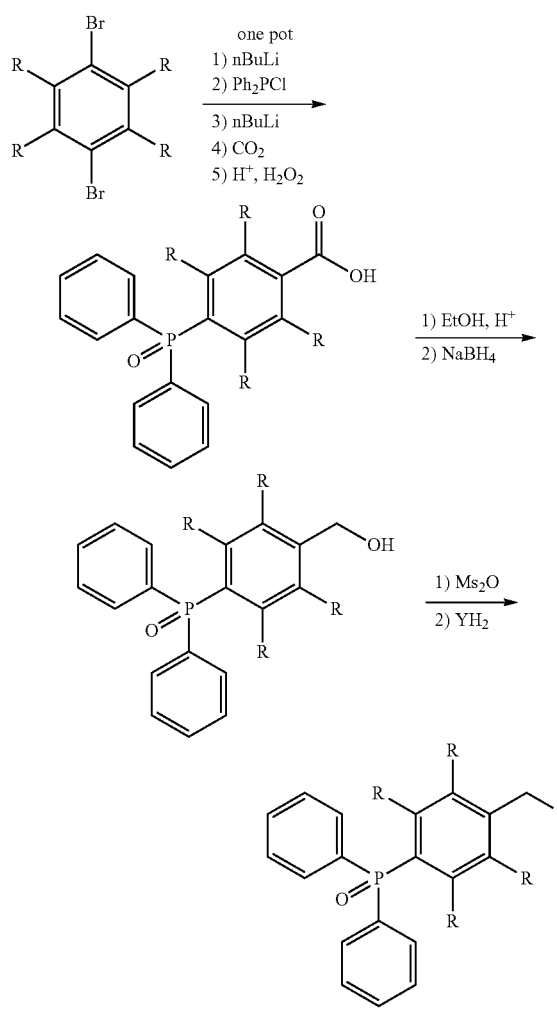

R = H, Me, or OMe
Y = S or NH wherein the protecting group is produced by reacting dibromide with butyllithium (nBuLi), diphenylchlorophosphine (Ph2PCl), carbon dioxide (CO2), and hydrogen peroxide (H+, H2O2) in a single reaction to produce a carboxylic acid product, isolating the carboxylic acid product, refluxing the carboxylic acid product in acidic ethanol (EtOH, H+), adding sodium borohydride (NaBH4) to form the alcohol product, and treating the alcohol product with mesic anhydride Ms2O or YH2; and wherein R is: H, Me, or OMe; and Y is: S or NH.

10

In another embodiment, protecting group:

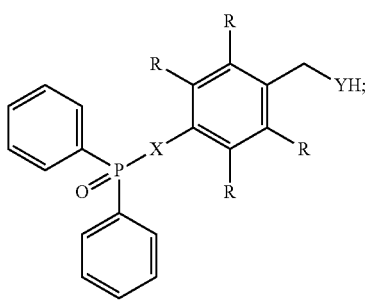

(1C)

is produced by the following:

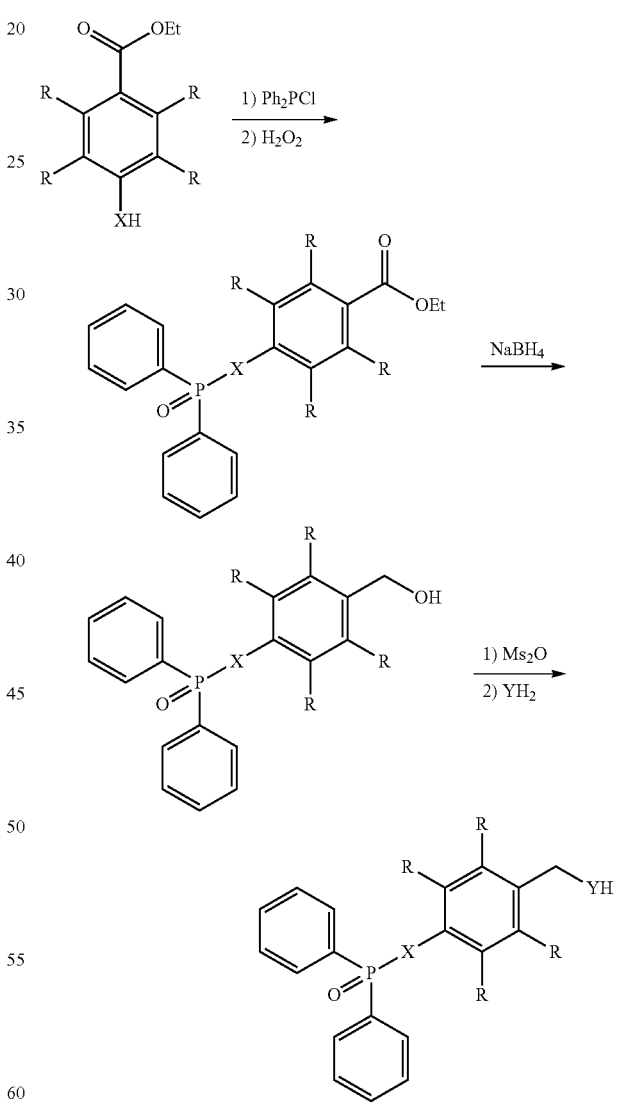

R = H, Me, OMe
X = O, S, NH
Y = O, S, NH wherein the ethyl ester derivative is reacted with diphenylchlorophosphine (Ph2PCl), followed by hydrogen peroxide (H2O2) for oxidation. The resulting phosphine oxide is treated with sodium borohydride (NaBH4) to produce the alcohol, which is treated with mesic anhydride (Ms2O) and YH2 to form (1C).; and wherein R is: H, Me, or OMe; X is: O, or NH; and Y is: O, S, or NH.

In another embodiment protecting group:

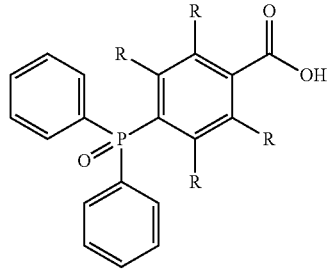

(1D)

is produced by the following:

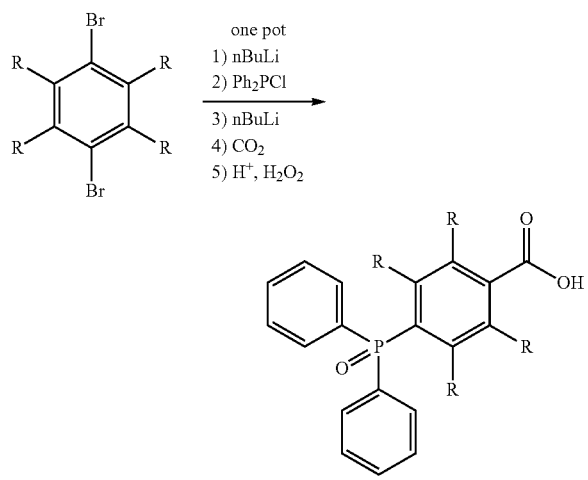

wherein the dibromide is reacted with butyllithium (nBuLi), diphenylchlorophosphine (Ph2PCl), carbon dioxide (CO2), and hydrogen peroxide (H+, H2O2) in a one-pot fashion to produce the carboxylic acid product (ID).; and wherein R is: H, Me, or OMe.

In another embodiment of the present invention, protecting group:

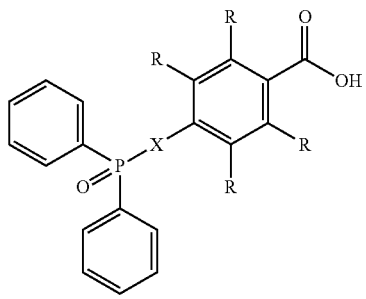

(1E)

is produced by the following:

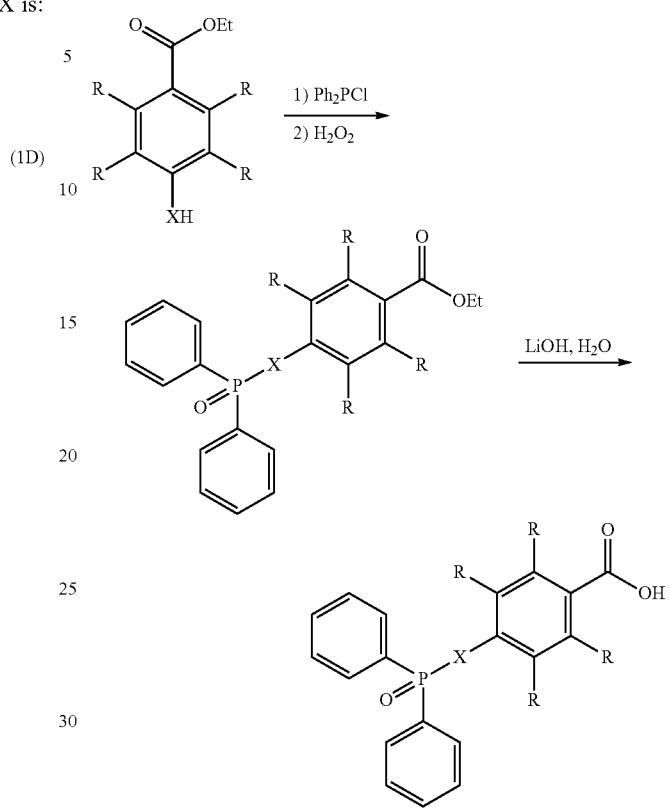

wherein the ethyl ester derivative is reacted with diphenylchlorophosphine (Ph2PCl), followed by hydrogen peroxide (H2O2) for oxidation. The resulting phosphine oxide is treated with lithium hydroxide (LiOH) and water (H2O), forming the carboxylic acid product (IE).; and wherein R is: H, Me, or OMe; and X is: O, S or NH.

In another embodiment of the present invention, a method of attaching a protecting group 1A, 1B, 1C, 1D, or 1E to an amino acid, wherein the method comprises reacting a protecting group of claim 1 with amino acid compound:

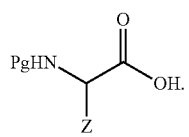

Such method may comprise the steps of:

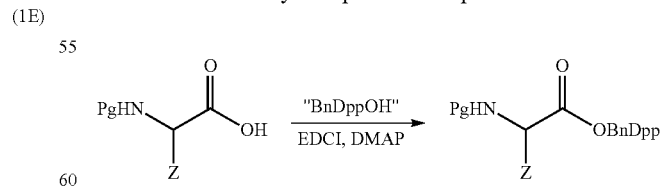

wherein BnDppOH is a protecting group (1A, 1B, 1C, 1D, or 1E); and wherein Pg may include, but is not limited to: Cbz, Fmoc, Boc, Bn, Fm, or tBu; and wherein Z is a general variable.

In another embodiment, a method of the present invention includes the protecting group:

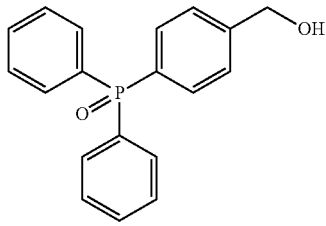
(1A)

The method may further comprise the steps of:

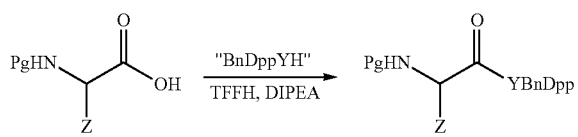

wherein BnDppYH is a protecting group (1A, 1B, 1C, 1D, or 1E); and wherein Pg may include but is not limited to: Cbz, Fmoc, Boc, Bn, Fm, or tBu; and wherein Z is a general variable.

In another embodiment of the present invention the method includes a protecting group:

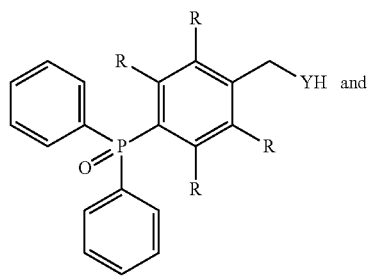
(1B)

and

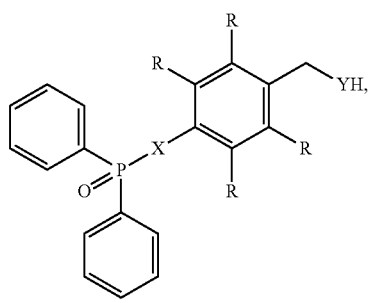
(1C)

wherein R is: H, Me, or OMe; and wherein X is: O, S, or NH.

In another embodiment the method comprises the steps of:

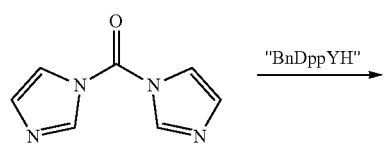

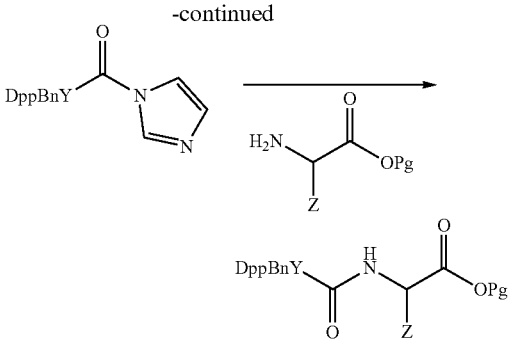

wherein BnDppYH is a protecting group 1A, 1B, 1C, 1D, or 1E; Pg may include but is not limited to: Cbz, Fmoc, Boc, Bn, Fm, or tBu; and wherein Z is a general variable.

In another embodiment, the method of the present invention comprises the steps of:

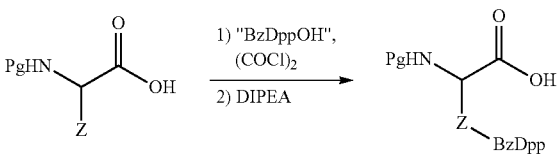

wherein BzDppOH is a protecting group 1A, 1B, 1C, 1D, or 1E; Pg may include but is not limited to: Cbz, Fmoc, Boc, Bn, Fm, or tBu; and Z is a general variable.

In another embodiment, the method comprises the protecting group:

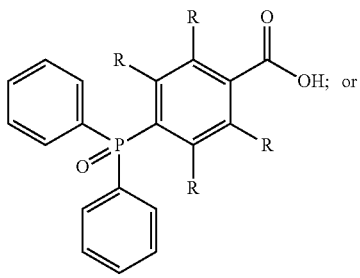
(1D)

or

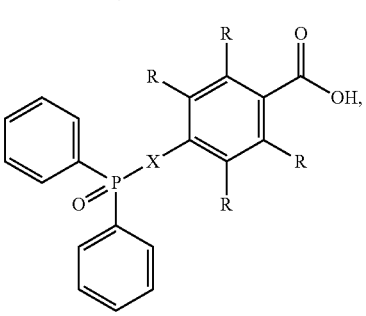
(1E)

wherein R is selected from the group consisting of: H, Me, or OMe; and wherein X is selected from the group consisting of: O, S, or NH.

In another embodiment of the present invention, a method of performing a Group Assisted Purification (GAP) peptide synthesis is provided, wherein the method comprises the steps of attaching a protecting group 1A, 1B, 1C, 1D, or 1E to an amino acid using any of the methods described herein and then Fmoc-tBu-based solution phase peptide synthesis (SolPPS) coupling reactions on the resulting products the methods described herein. Such method of GAP-PS may further include the reaction occurring in ethyl acetate, or alternatively in dichloromethane.

The principles discussed herein may be embodied in many different forms. The preferred embodiments of the present disclosure will now be described where for completeness, reference should be made at least to the Figures.

Example 1

Figure 5:
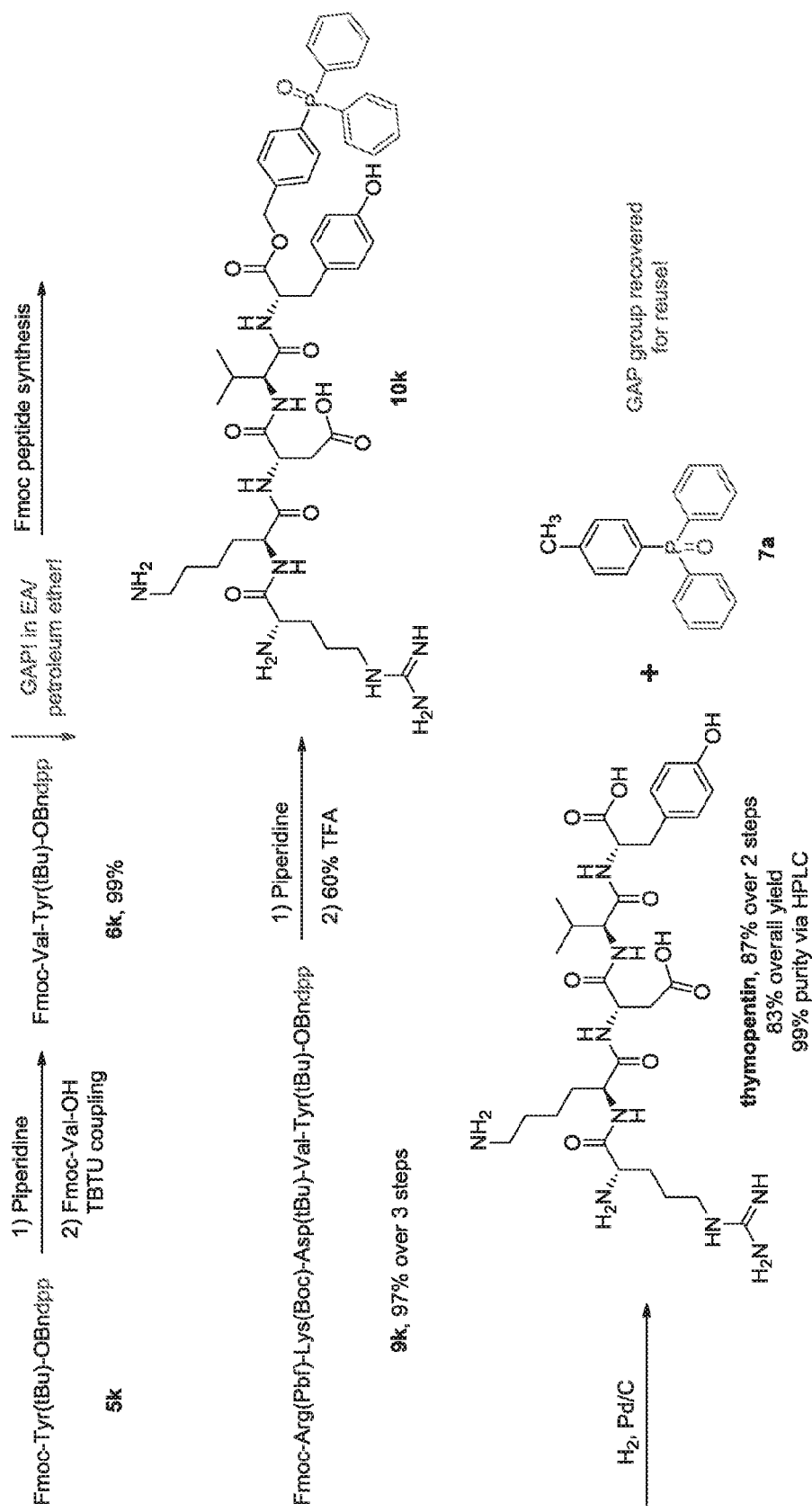
FIG. 5 depicts a schematic for the synthesis of thymopentin using the protecting group of FIG. 2 for purposes of the exemplary non-limiting example of peptide synthesis of the present invention.

For a first application of a new protecting group, capabilities in handling an Fmoc/tBu SolPPS strategy are tested. The target peptide of interest for this non-limiting example is thymopentin, a pharmacologically interesting, biologically active pentapeptide subunit of the immunomodulatory polypeptide, thymopoietin. For a short peptide, thymopentin contains amino acids with a variety of functional groups (1 aromatic, two basic (one with guanidine), two acidic, and one β-branched). This makes thymopentin an ideal candidate for an exemplary use of a GAP protecting group and its ability to tolerate the removal of several side-chain protecting groups. Synthesis of thymopentin is illustrated in FIG. 5. Compound 5k is first treated with 30% piperidine in DCM for 10 minutes to remove the Fmoc group, followed by ammonium chloride wash to remove the excess piperidine. The DCM layer (after drying) is directly loaded with the next Fmoc ammo acid (side chain protection as noted), along with TBTU coupling reagent and DIPEA. After coupling for 20 minutes, the reaction mixture is washed with ammonium chloride and 0.5 M sodium hydroxide (respectively), dried and evacuated. The crude product after coupling contains several impurities, most notably NFMP and tetramethyl urea (from coupling). The GAP purification procedure can easily remove these impurities simply by dissolving the mixture in a minimal amount of ethyl acetate, followed by selective precipitation of the GAP-peptide with petroleum ether. For the tetra- and pentapeptide fragments, a small amount of DCM is added to the ethyl acetate prior to precipitation, to help with the solubility. Following the last coupling step and the synthesis of 9k, the last Fmoc group is removed as before but after workup, the DCM layer is concentrated and the peptide is dissolved in TFA/DCM/H$_2$O (6/3/1) solution for side-chain deprotection. The pentapeptide 10k (now with Bndpp as the only protecting group) is precipitated using diethyl ether. This peptide is then subjected to hydrogenation and the GAP group removed. The product is isolated via extraction from chloroform with 10% acetic acid (aq). The product is isolated via extraction from chloroform with 10% acetic acid (aq). Unexpectedly, HPLC analysis of the product peptide reveals that the compound is nearly 99% pure without any column chromatography, recrystallization, or polymer supports. The GAP group can be recovered simply by evacuating the chloroform layer after extraction. Subjecting this raw material to the synthesis methods in FIG. 2 can regenerate BndppOH General Methods:

All solvents were ACS grade and used without additional purification. FIRMS analysis was performed using an Orbitrap mass analyzer. HPLC analysis was conducted using a Perkin Elmer Flexar isocratic pump equipped with a UV detector. Fmoc and Boc protected amino acids were purchased from BachemBio and used directly for coupling.

Synthesis of Benzoic Acid 2:

10.0 g 1 was placed in a 500 mL round-bottomed flask, followed by 130 mL 0.43 M NaOH(aq) solution and then 22.2 g KMnO$_4$. The reaction was stirred at reflux for 12 hours, after which the reaction mixture was filtered through celite while hot. The resulting solution was washed X2 with diethyl ether, followed by the addition of 50% H$_2$SO$_4$ to precipitate the product. After filtration, benzoic acid 2 was collected as a white solid; yield, 10.8 g, 93%; this product was directly subjected to the next reaction.

Synthesis of Ester 3:

10.8 g 2 was placed in a 500 mL round-bottomed flask along with 300 mL ethanol and 3 mL thionyl chloride. The reaction was brought to reflux and stirred for 12 hours. After completion, the reaction was cooled to room temperature and the volatiles evacuated, affording ester 3 as a white solid; yield, 11.8 g, 99%; this product was directly subjected to the next reaction.

Synthesis of BndppOH 4:

11.8 g ester 3 was placed in a 500 mL round-bottomed flask along with 300 mL ethanol. The reaction was cooled to 0° C., after which 3.82 g NaBH$_4$ was added portionwise. The reaction was brought to room temperature and stirred for 12 hours. The solvent was evacuated, followed by solvation of the crude in DCM and washing X3 with 2 M HCl(aq). The organic layer was then dried over MgSO$_4$, filtered, and evacuated to afford BndppOH 4 as a white solid; yield, 9.96 g, 96%; this compound has been previously synthesized via a different method, and NMR data matches that found in the literature[30]: $^1$H NJVIR (400 MHz, CDCl$_3$) δ=7.62-7.57 (m, 4H), 7.54-7.47 (m, 4H), 7.45-7.40 (m, 4H), 7.38-7.36 (m, 2H), 4.70 (s, 2H).

General Procedure for Bndpp Protection:

100 mg BndppOH, 2.0 eq PG-AA-OH, and 10 mL DCM were stirred at 0° C. in a 20 mL screw-cap vial. 124 mg (2.0 eq) EDCI(HCl) was added, and the reaction was stirred for 10 min, at which point 4 mg (10 mol %) DMAP was added and the reaction was brought to room temp and stirred for 2 hours. The reaction mixture was washed X2 with sat. NH$_4$Cl(aq), followed by sat. Na$_2$CO$_3$(aq) X2. The combined organic layers were dried with MgSO$_4$, filtered, and evacuated to afford the crude protected amino acid. GAP purification was performed by dissolving the crude mixture in a minimal amount of ethyl acetate, followed by precipitation with petroleum ether and filtration of the resulting white precipitate. This same procedure was used for every substrate except 5k, where the reaction was conducted on a larger scale using 600 mg BndppOH and the same equivalents of the other reagents as before.

Compound Legend

Compound 5a. White solid; yield 180 mg, 99%; mp 62-63° C.; $^1$H NMR (400 MHz, CDCl3) δ=7.69-7.63 (m, 6H), 7.58-7.52 (m, 2H), 7.49-7.45 (m, 4H), 7.35-7.32 (m, 2H), 7.24-7.18 (m, 3H), 7.07-7.05 (d, J=6.4 Hz, 2H), 5.20-5.12 (m, 2H), 4.96-4.95 (d, J=7.8 Hz, 1H), 4.68-4.58 (m, 1H), 3.09-3.07 (d, J=5.9 Hz, 2H), 1.40 (s, 9H); $^{13}$C NMR (100 MHz, CDCl$_3$) δ=171.9, 155.2, 139.3, 135.9, 133.0, 132.6, 132.5, 132.2, 132.1, 132.0, 129.4, 128.8, 128.6, 128.2, 128.1, 127.2, 80.2, 66.3, 54.6, 38.5, 28.4; $^{31}$P NMR (162 MHz, CDCl$_3$) δ=29.28; HRMS (ESI): m/z calcd for [C$_{33}$H$_{34}$NO$_5$P+H]$^+$: 556.2253, found: 556.2235.

Compound 5b. White solid; yield 189 mg, 99%; mp 76-77° C.; $^1$H NMR (400 MHz, CDCl$_3$) δ=7.69-7.64 (m, 6H), 7.58-7.54 (m, 2H), 7.49-7.44 (m, 6H), 6.65 (bs, 1H), 5.52-5.50 (d, J=5.9 Hz, 1H), 5.27-5.19 (m, 2H), 4.54 (bs, 1H), 4.38-4.32 (m, 2H), 3.09-2.91 (m, 2H), 2.06-2.00 (m, 1H), 1.98 (s, 3H), 1.43 (s, 9H); $^{13}$C NMR (100 MHz, CDCl$_3$) δ=170.9, 170.4, 139.3, 133.5, 132.8, 132.6, 132.5, 132.4, 132.2, 132.1, 131.8, 128.7, 128.2, 80.7, 66.7, 54.2, 42.2, 34.5, 28.4, 23.3, 22.5, 14.2; $^{31}$P NMR (162 MHz, CDCl$_3$) δ=29.46; HRMS (ESI): m/z calcd for [C$_{30}$H$_{35}$N$_2$O$_6$PS+H]$^+$: 583.2032, found: 583.2012.

Compound 5c. White solid; yield 246 mg, 99%; mp 86-87° C.; $^1$H NMR (400 MHz, CDCl$_3$) δ=7.76-7.74 (d, J=7.5 Hz, 2H), 7.69-7.63 (m, 6H), 7.60-7.52 (m, 4H), 7.47-7.42 (m, 6H), 7.40-7.36 (t, J=7.4 Hz, 2H), 7.31-7.27 (t, J=7.4 Hz, 2H), 5.48-5.46 (d, J=7.3 Hz, 1H), 5.22 (s, 2H), 4.65-4.57 (bs, 1H), 4.43-4.34 (m, 3H), 4.22-4.19 (t, J=6.9 Hz, 1H), 3.10-3.02 (m, 2H), 1.88-1.84 (m, 1H), 1.72-1.68 (m, 1H), 1.42 (s, 9H), 1.38-1.24 (m, 4H); $^{13}$C NMR (100 MHz, CDCl$_3$) δ=172.4, 156.2, 143.9, 141.4, 139.5, 132.9, 132.6, 132.2, 131.8, 128.7, 128.0, 127.8, 127.2, 125.2, 120.1, 79.3, 67.2, 66.4, 54.0, 47.3, 40.0, 32.1, 29.8, 28.5, 22.5; $^{31}$P NMR (162 MHz, CDCl$_3$) δ=29.37; HRMS (ESI): m/z calcd for [C$_{45}$H$_{47}$N$_2$O$_7$P+H]$^+$: 759.3199, found: 759.3183.

Compound 5d. White solid; yield 227 mg, 99%; mp 85-86° C.; $^1$H NMR (400 MHz, CDCl$_3$) δ=7.76-7.74 (d, J=7.5 Hz, 2H), 7.66-7.52 (m, 10H), 7.46-7.36 (m, 8H), 7.29-7.26 (t, J=7.2 Hz, 2H), 5.86-5.84 (d, J=8.6 Hz, 1H), 5.29-5.20 (dd, J=12.8 Hz, 12.4 Hz, 2H), 4.69-4.66 (m, 1H), 4.44-4.31 (m, 2H), 4.24-4.21 (t, J=7.0 Hz, 1H), 3.01-2.95 (dd, J=4.3 Hz, 17.0 Hz, 1H), 2.81-2.76 (dd, J=4.2 Hz, 17.0 Hz, 1H), 1.39 (s, 9H); $^{13}$C NMR (100 MHz, CDCl$_3$) δ=170.9, 170.2, 156.1, 143.9, 143.8, 141.4, 139.5, 132.7, 132.6, 132.5, 132.2, 132.1, 131.7, 128.7, 128.6, 128.0, 127.9, 127.2, 125.2, 120.1, 82.1, 67.4, 66.7, 50.7, 47.2, 37.8, 28.1; $^{31}$P NMR (162 MHz, CDCl$_3$) δ=29.75; HRMS (ESI): m/z calcd for [C$_{42}$H$_{40}$NO$_7$P+H]$^+$: 702.2621, found: 702.2602.

Compound 5e. White solid; yield 257 mg, 97%; mp 98-99° C.; $^1$H NMR (400 MHz, CDCl$_3$) δ=8.10-8.08 (d, J=7.7 Hz, 1H), 7.76-7.74 (d, J=7.5 Hz, 2H), 7.68-7.61 (m, 6H), 7.56-7.36 (m, 14H), 7.31-7.25 (m, 3H), 7.21-7.18 (t, J=7.5 Hz, 1H), 5.48-5.46 (d, J=8.2 Hz, 1H), 5.21-5.06 (dd, J=12.9 Hz, 47.8 Hz, 2H), 4.84-4.79 (m, 1H), 4.41-4.34 (m, 2H), 4.22-4.18 (t, J=7.0 Hz, 1H), 3.28-3.27 (d, J=5.7 Hz, 2H), 1.63 (s, 9H); $^{13}$C NMR (100 MHz, CDCl$_3$) δ=171.6, 155.8, 149.6, 143.9, 143.8, 141.4, 139.1, 135.5, 132.9, 132.6, 132.5, 132.2, 132.1, 131.8, 130.4, 128.7, 128.6, 127.8, 127.2, 125.2, 124.8, 124.3, 122.8, 120.1, 118.9, 115.5, 114.8, 84.0, 67.4, 66.6, 54.3, 47.2, 28.2; $^{31}$P NMR (162 MHz, CDCl$_3$) δ=29.32; HRMS (ESI): m/z calcd for [C$_{50}$H$_{45}$N$_2$O$_7$P+H]$^+$: 817.3043, found: 817.3031.

Compound 5f. White solid; yield 304 mg, 99%; mp 117-118° C.; $^1$H NMR (400 MHz, CDCl$_3$) δ=7.75-7.73 (d, J=7.5 Hz, 2H), 7.69-7.63 (m, 4H), 7.60-7.55 (m, 4H), 7.53-7.46 (m, 8H), 7.39-7.35 (t, J=7.4 Hz, 2H), 7.29-7.27 (d, J=7.4 Hz, 2H), 6.61 (bs, 2H), 5.88 (bs, 1H), 5.50-5.35 (dd, J, =9.7 Hz, J2=52.8 Hz, 2H), 5.03-5.00 (d, J=11.8 Hz, 1H), 4.36-4.34 (m, 3H), 4.20-4.16 (t, J=7.0 Hz, 1H), 3.25-3.15 (m, 2H), 2.90 (s, 2H), 2.78-2.67 (m, 2H), 2.58 (s, 3H), 2.51 (s, 3H), 2.06 (s, 3H), 1.68-1.57 (m, 2H), 1.42 (s, 6H); $^{13}$C NMR (100 MHz, CDCl$_3$) δ=172.0, 158.6, 156.6, 156.2, 143.8, 141.3, 140.0, 138.3, 133.3, 132.5, 132.4, 132.2, 132.0, 131.9, 131.8, 130.8, 128.9, 128.8, 127.8, 127.2, 125.2, 124.6, 121.1, 120.0, 119.8, 117.4, 86.4, 68.0, 67.2, 66.2, 53.5, 47.1, 43.3, 40.5, 29.6, 28.6, 25.2, 19.4, 18.1, 12.6; $^{31}$P NMR (162 MHz, CDCl$_3$) δ=31.03; HRMS (ESI): m/z calcd for [C$_{53}$H$_{55}$N$_4$O$_8$PS+H]$^+$: 939.3556, found: 939.3538.

Compound 5g. White solid; yield 204 mg, 99% mp 81-82° C.; $^1$NMR (400 MHz, CDCh) δ=7.77-7.75 (d, J=7.2 Hz, 2H), 7.70-7.53 (m, 10H), 7.48-7.44 (m, 6H), 7.41-7.37 (t, J=7.2 Hz, 2H), 7.32-7.28 (t, J=7.2 Hz, 2H), 5.36-5.34 (d, J=8.8 Hz, 1H), 5.22 (s, 2H), 4.44-4.32 (m, 3H), 4.24-4.21 (t, J=6.8 Hz, 1H), 2.26-2.17 (m, 1H), 0.97-0.95 (d, J=6.8 Hz, 3H); $^{13}$C NMR (100 MHz, CDCl$_3$) δ=172.0, 156.3, 143.9, 143.8, 141.4, 139.4, 132.6, 132.5, 132.2, 132.1, 128.7, 128.6, 128.1, 128.0, 127.8, 127.1, 125.1, 120.1, 67.1, 66.2, 59.1, 47.2, 31.3, 19.1, 17.6; $^{31}$P NMR (162 MHz, CDCl$_3$) δ=29.45; HRMS (ESI): m/z calcd for [C$_{39}$H$_{36}$NO$_5$P+H]$^+$: 630.2409, found: 630.2392.

Compound 5h. White solid; yield 287 mg, 99%; mp 121-122° C.; $^1$H NMR (400 MHz, CDCl$_3$) δ=7.76-7.71 (t, J=6.4 Hz, 2H), 7.65-7.51 (m, 12H), 7.46-7.40 (m, 4H), 7.38-7.31 (m, 4H), 7.24-7.20 (m, 9H), 7.15-7.13 (m, 6H), 6.75 (s, 1H), 6.13-6.11 (d, J=8.8 Hz, 1H), 5.21-5.11 (q, J=12.8 Hz, 2H), 4.69-4.65 (m, 1H), 4.43-4.38 (m, 1H), 4.30-4.26 (t, J=8.9 Hz, 1H), 4.20-4.16 (t, J=7.1 Hz, 1H), 3.18-3.13 (dd, J$_1$=4.2 Hz, J$_2$=15.8 Hz, 1H), 2.87-2.82 (dd, J$_1$=4.2 Hz, J$_2$=15.8 Hz, 1H); $^{13}$C NMR (100 MHz, CDCl$_3$) δ=171.0, 169.4, 156.4, 144.3, 144.0, 143.8, 141.4, 139.6, 132.6, 132.5, 132.2, 132.0, 128.7, 128.6, 128.2, 127.9, 127.6, 127.5, 127.4, 127.2, 125.3, 120.1, 71.1, 67.4, 66.6, 51.2, 47.2, 38.8; $^{31}$P NMR (162 MHz, CDCl$_3$) δ=29.38; HRMS (ESI): m/z calcd for C$_5$H$_{47}$N$_2$O$_6$P+H]$^+$: 887.3250, found: 887.3230.

Compound 5i. White solid; yield 195 mg, 99%; mp 78-79° C.; $^1$H NMR (400 MHz, CDCl$_3$) δ=7.76-7.75 (d, J=7.6 Hz, 2H), 7.70-7.63 (m, 6H), 7.59-7.53 (m, 4H), 7.48-7.37 (m, 8H), 7.31-7.28 (t, J=7.6 Hz, 2H), 5.37-5.35 (d, J=7.6 Hz, 1H), 5.23 (s, 2H), 4.49-4.38 (m, 3H), 4.23-4.19 (t, J=7.2 Hz, 1H), 1.46-1.44 (d, J=7.2 Hz, 3H); $^{13}$C NMR (100 MHz, CDCl$_3$) δ=172.9, 155.8, 144.0, 143.8, 141.4, 139.5, 132.9, 132.6, 132.5, 132.2, 132.1, 131.9, 128.7, 128.6, 127.9 127.8, 127.2, 125.2, 120.1, 67.2, 66.4, 53.6, 49.8, 47.3, 31.7, 22.8, 18.7, 14.3; 31P NMR (162 MHz, CDCl$_3$) δ=29.28; HRMS (ESI): m/z calcd for [C$_{37}$H$_{32}$NO$_5$P+H]$^+$: 602.2096, found: 602.2080.

Compound 5j. White solid; yield 189 mg, 99%; mp 79-80° C.; $^1$H NMR (400 MHz, CDCl$_3$) δ=7.76-7.75 (d, J=7.5 Hz, 2H), 7.70-7.63 (m, 6H), 7.60-7.53 (m, 4H), 7.48-7.42 (m, 6H), 7.41-7.37 (t, J=7.5 Hz, 2H), 7.31-7.27 (t, J=7.4 Hz, 2H), 5.42-5.37 (m, 1H), 5.23 (s, 2H), 4.41-4.39 (d, J=7.1 Hz, 2H), 4.24-4.21 (t, J=7.0 Hz, 1H), 4.06-4.05 (d, J=5.6 Hz, 2H); $^{13}$C NMR (100 MHz, CDCl3) δ=169.9, 156.4, 143.9, 141.4, 139.3, 132.9, 132.6, 132.2, 132.1, 131.8, 128.7, 128.6, 128.1, 128.0, 127.9, 127.2, 125.2, 120.1, 67.4, 66.4, 47.2, 42.9; $^{31}$P NMR (162 MHz, CDCl$_3$) δ=29.33; HRMS (ESI): m/z calcd for [C$_{36}$H$_{32}$NO$_5$P+H]$^+$: 588.1940, found: 588.1925.

Compound 5k. White solid; yield, 99%; mp 99-100° C.; $^1$H NMR (400 MHz, CDCl$_3$) δ=7.77-7.75 (d, J=7.6 Hz, 2H), 7.69-7.64 (m, 6H), 7.56-7.53 (t, J=7.4 Hz, 4H), 7.48-7.44 (m, 4H), 7.41-7.36 (m, 4H), 7.31-7.27 (t, J=7.4 Hz, 2H), 6.95-6.93 (d, J=8.4 Hz, 2H), 6.87-6.85 (d, J=8.4 Hz, 2H), 5.28-5.26 (d, J=7.9 Hz, 1H), 5.22-5.13 (q, J=8.5 Hz, 2H), 4.70-4.68 (m, 1H), 4.44-4.32 (m, 2H), 4.21-4.18 (t, J=6.9 Hz, 1H), 3.09-3.06 (m, 2H), 1.30 (s, 9H); $^{31}$C NMR (100 MHz, CDCl$_3$) δ=171.5, 155.7, 154.7, 143.9, 143.8, 141.4, 139.2, 132.9, 132.6, 132.5, 132.2, 132.1, 129.9, 128.8, 128.6, 128.2, 128.0, 127.9, 127.2, 125.2, 124.3, 120.1, 78.6, 67.1, 66.5, 55.0, 47.3, 37.8, 28.9; $^{31}$P NMR (162 MHz, CDCl$_3$) δ=29.29; HRMS (ESI): m/z calcd for [C$_{47}$H$_{44}$NO$_6$P+H]$^+$: 750.2984, found: 750.2966.

Synthesis of compound 6a: Boc-Phe-OBndpp 5a (80 mg) was dissolved in 5 mL 60% TFA/DCM and stirred at room temperature. After 1 hour, the solvent mixture was evacuated, and the crude dissolved in DCM. After washing X2 with 1 M Hel(aq), the organic layer was dried with MgSO$_4$, filtered, and concentrated to afford crude 6a Hel salt. GAP purification was conducted by dissolving the crude in a minimal amount of ethyl acetate, followed by precipitation with petroleum ether. The purified product was isolated via filtration as a white solid; yield 71 mg, 99%; mp 68-71° C. (decomposition); $^1$H NMR (400 MHz, CDCl$_3$) δ=7.57-7.40 (m, 12H), 7.10-7.04 (m, 7H), 4.99-4.96 (d, J=10.4 Hz, 2H), 4.41 (bs, 1H), 3.43 (bs, 1H), 3.25 (bs, 1H); $^{13}$C NMR (100 MHz, CDCl$_3$) δ=169.1, 138.6, 134.3, 132.5, 132.3, 132.2, 132.1, 132.0, 131.5, 129.6, 128.8, 128.7, 128.6, 128.3, 128.2, 127.5, 67.0, 54.6, 36.6; $^{31}$P NMR (162 MHz, CDCl$_3$) δ=29.79; HRMS (ESI): m/z calcd for [C$_{28}$H$_{26}$NO$_3$P+H]$^+$: 456.1729, found: 456.1725.

Synthesis of HBndpp 7a: Boc-Phe-OBndpp 5a (100 mg) was dissolved in a 5 mL mixture of methanol and 10% Pd/C (20 mg). The reaction mixture was placed under H$_2$ atmosphere (balloon) and stirred at room temperature for 12 hours. The reaction mixture was then filtered through celite and the methanol evacuated. The crude solid was dissolved in DCM and washed X2 with sat. Na$_2$CO$_3$(aq) solution. The organic layer was dried over MgSO$_4$, filtered, and evacuated to afford HBndpp 7a as a white solid; yield, 51 mg, 97%; this compound has been previously synthesized via a different method, and NMR data matches that found in the literature$^{30}$: $^1$H NMR (400 MHz, CDCl$_3$) δ=7.68-7.63 (m, 4H), 7.57-7.52 (m, 4H), 7.48-7.44 (m, 4H), 7.29-7.26 (m, 2H), 2.41 (s, 3H).

General procedure for Fmoc deprotection and coupling: Fmoc-(AA)n-OBnDpp dissolved in 30% Piperidine/DCM (100 mL per gram), and stirred at room temperature for 10 minutes. Reaction mixture washed X3 with sat. NH$_4$Cl(aq), dried over MgSO$_4$, and filtered. To the resulting DCM solution was added 1.2 eq TBTU, 1.2 eq Fmoc-AA-OH, and 2.4 eq DIPEA; the coupling reaction was stirred for 20 min. The reaction mixture was then washed X2 with sat. NH$_4$Cl (aq), followed by 0.5 M NaOH X2. The combined organic layers were dried over MgSO$_4$, filtered, and evacuated to afford the crude peptide. GAP purification was performed by dissolving the crude mixture (containing Fmoc-(AA)$_{n+1}$-OBndpp, NFMP, and tetramethylurea) in a minimal amount of ethyl acetate (with some DCM for longer peptides), followed by precipitation of the product with petroleum ether. The product peptide was removed via vacuum filtration as a white solid in quantitative yield.

Compound 9k, Fmoc-Arg(Pbf)-Lys(Boc)-Asp(tBu)-Val-Tyr(tBu)-OBndpp. White solid; yield 3.08 g, 97% (over 3 steps from 6k); mp 124-125° C.; Retention time on analytical NP-HPLC with 0.1% ethanolamine in IPA as the eluent: 8.85 min, 92.0% purity; HRMS (ESI): m/z calcd for [C$_{90}$H$_{114}$N$_9$O$_{17}$PS+H]$^+$: 1657.7903, found: 1657.7871.

Deprotection of side-chain protecting groups: Fmoc-Arg (Pbf)-Lys(Boc)-Asp(tBu)-Val-Tyr(tBu)-OBnDpp 9k was dissolved in 100 mL 30% Piperidine/DCM and stirred at room temp for 10 minutes. The reaction mixture was then washed X2 with saturated NH$_4$Cl(aq), dried over MgSO$_4$, filtered and evacuated. The crude was then dissolved in TFA/DCNI/H$_2$O (6/3/1) and stirred at room temp for 1 hour. The reaction mixture was evacuated to saturation, and then the product peptide precipitated with diethyl ether. Peptide 10k was obtained after filtration as a white solid and directly used for the next step.

Deprotection of BnDpp: To 100 mg dry Pd/C in a hydrogenation bottle was added H-RKDVY-OBnDpp 10k in 150 mL methanol. The bottle was placed under 70 PSI H$_2$ atmosphere and shaken at room temperature for 24 hours. The reaction mixture was filtered through celite, and evacuated to dryness. The crude was dissolved in a mixture of 10% acetic acid (aq) and chloroform, after which the aqueous layer was washed X2 with chloroform. Evacuation of the aqueous layer afforded thymopentin as a white solid; yield, 1.09 g, 87%; Retention time on analytical RP-HPLC with 50% MeCN in 0.06% TFA/H$_2$O as the eluent: 1.24 min, 98.9% purity; HRMS (ESI): m/z calcd for [C$_{30}$H$_{49}$N$_9$O$_9$+H]$^+$: 680.3731, found: 680.3730.o our delight, HPLC analysis of the product peptide reveals that the compound is nearly 99% pure without any column chromatography, recrystallization, or polymer supports. The GAP group can be recovered simply by evacuating the chloroform layer after extraction. Subjecting this raw material to the synthesis methods in FIG. 2 can regenerate BndppOH.

Further GAP Groups and Attachment Methods

Figure 6:
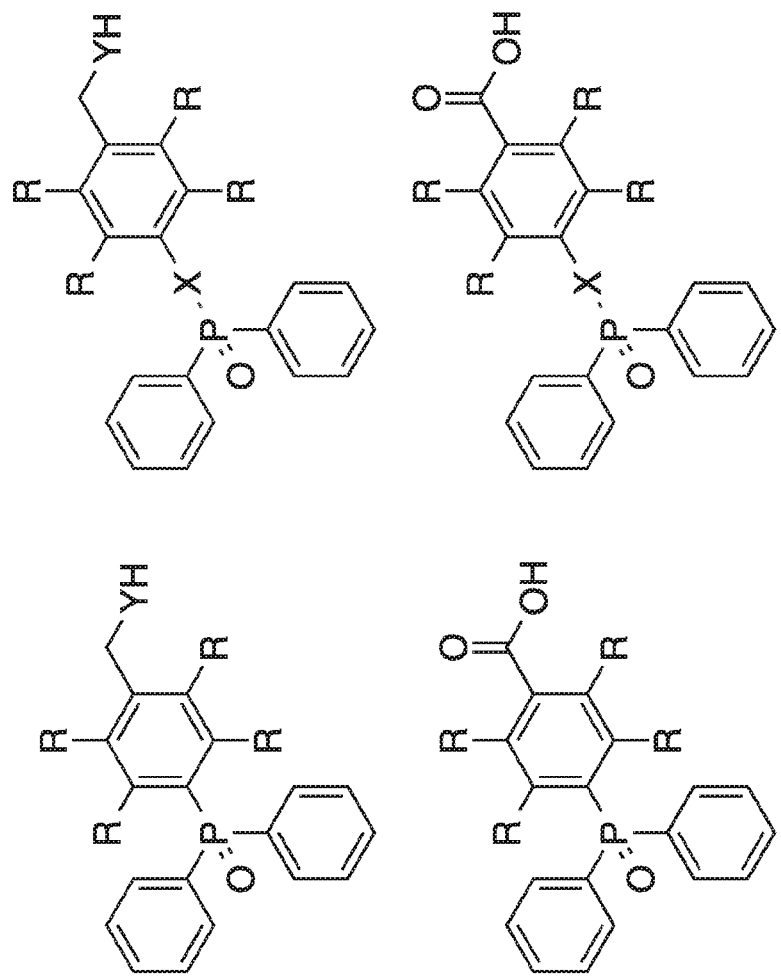
FIG. 6 depicts other protecting groups that can be use in embodiments of the present invention.
Figure 7:
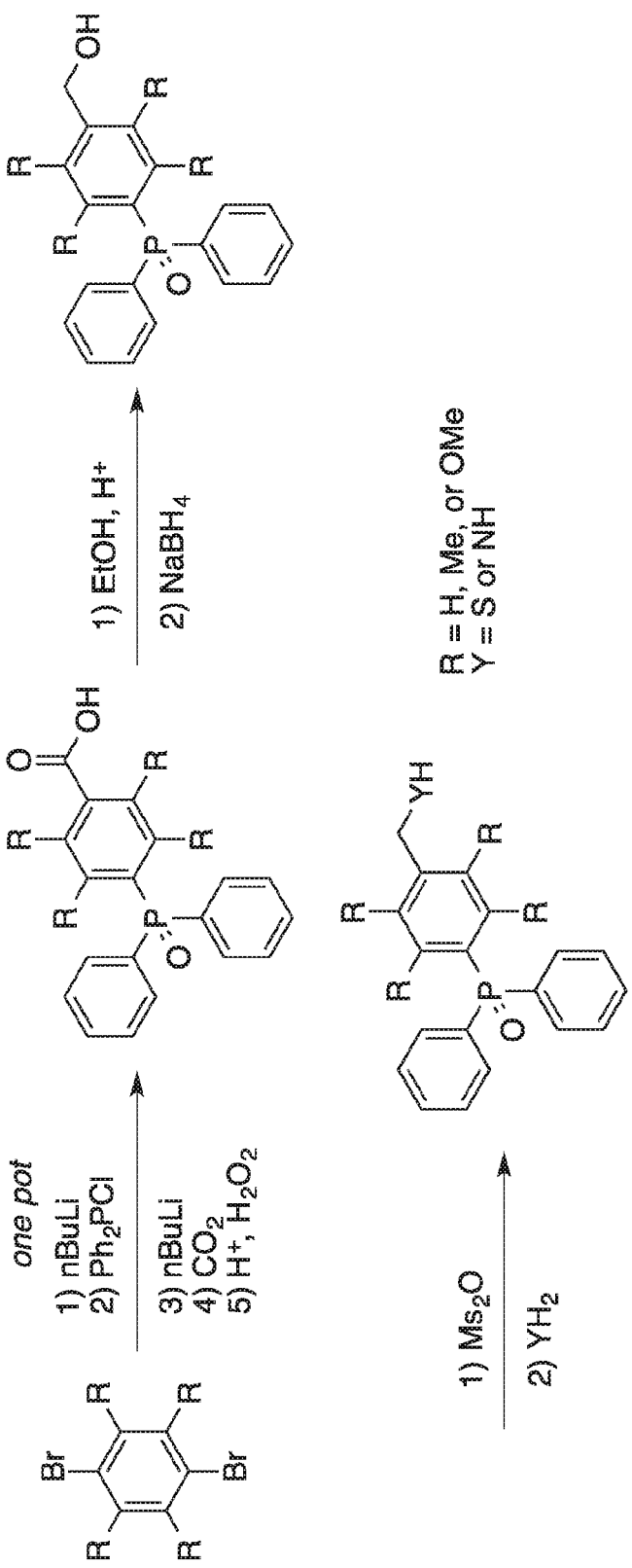
FIG. 7 depicts an alternative process for production, synthesis and manufacture of the protecting groups of FIG. 6 as utilized in embodiments of the present invention.
Figure 8:
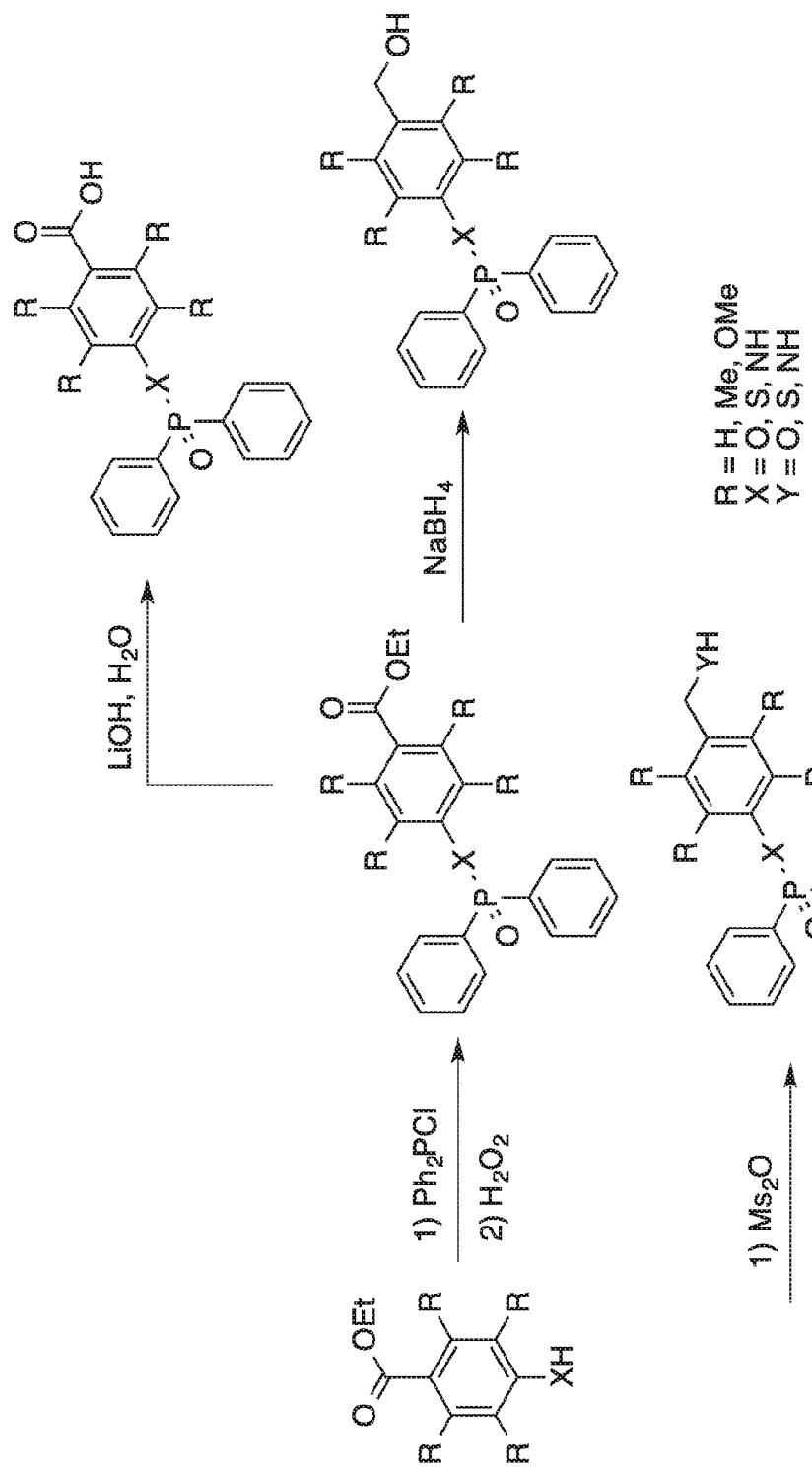
FIG. 8 depicts another alternative process for production, synthesis and manufacture of protecting groups of FIG. 6 as utilized in embodiments of the present invention.

FIG. 6 depicts representative protecting groups that can be used in embodiments of the present invention. FIGS. 7-8 depict alternative processes that can be used to develop BndppOH (alternative of the process shown in FIG. 2) and to develop other representative protecting groups, such as set forth in FIG. 6.

Figure 9A:
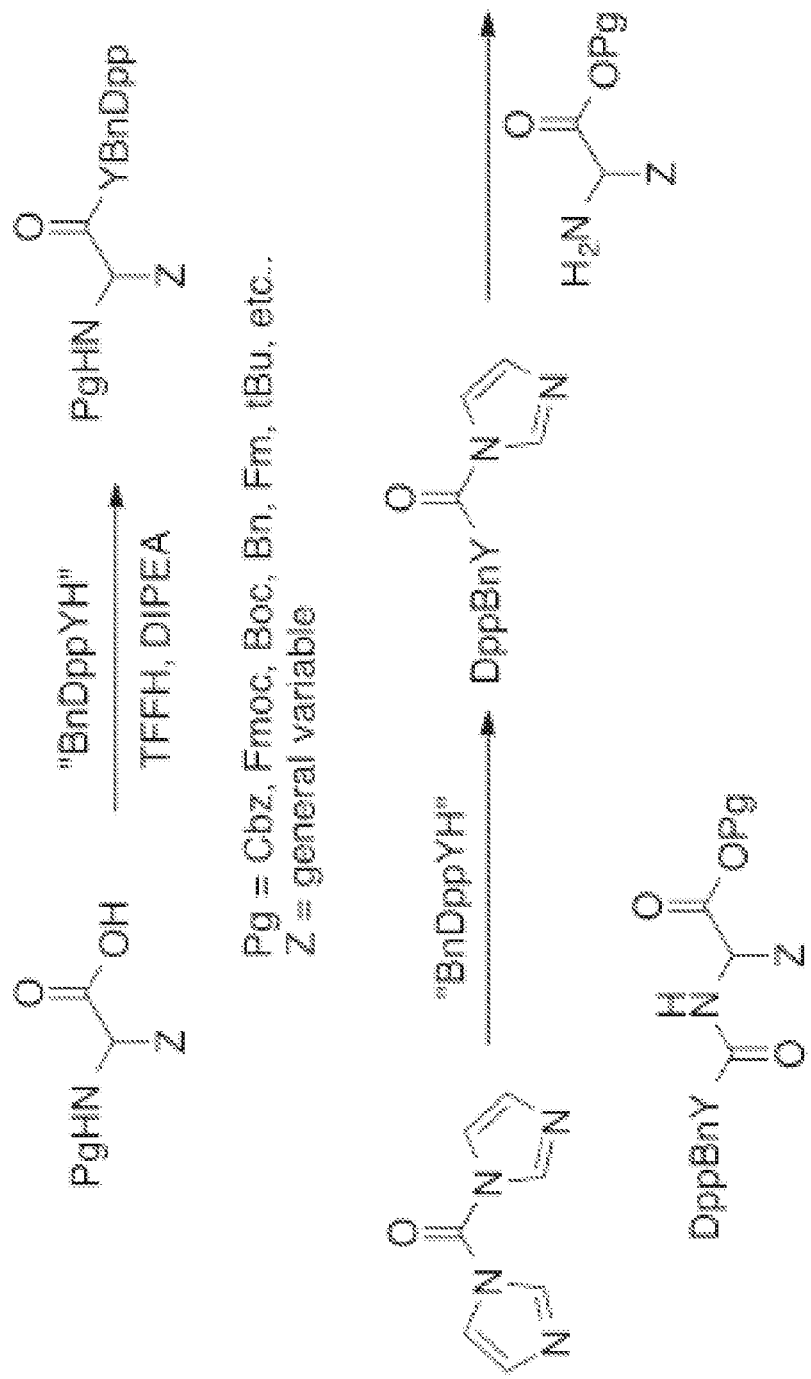
FIG. 9A depicts a schematic for the process of attaching the protecting group of "BnDppYH" to various amino acids.
Figure 9B:
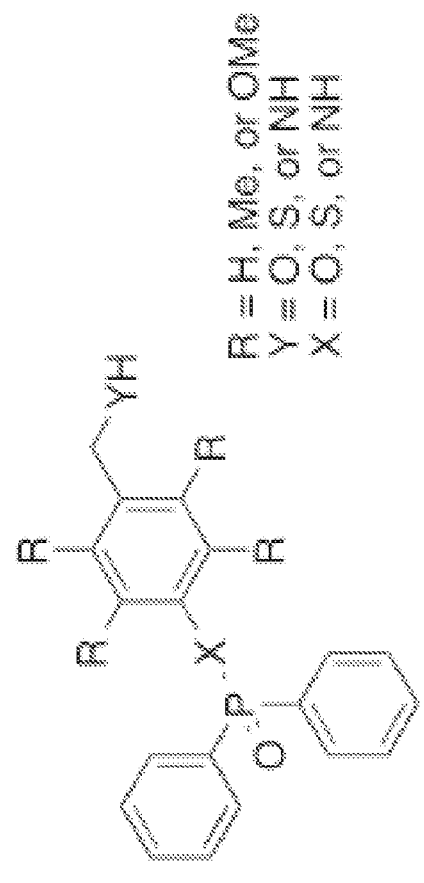
FIG. 9B depicts the protecting group "BnDppYH" utilized in the schematic for the process shown in FIG. 9A.
Figure 9B:
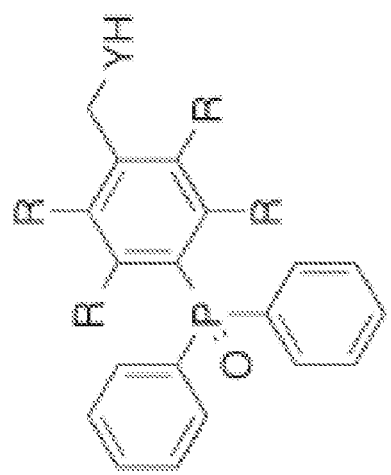
Figure 10A:
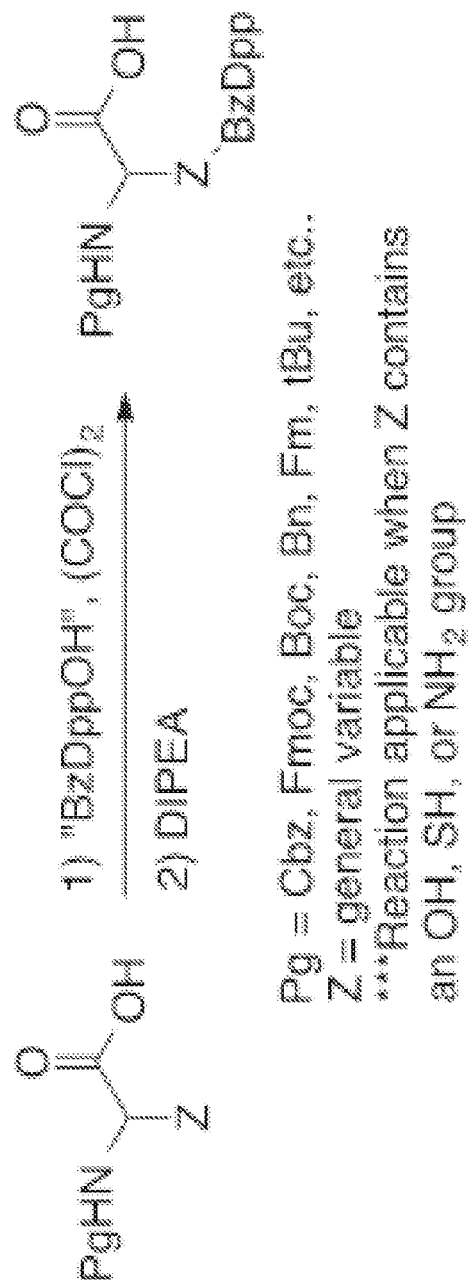
FIG. 10A depicts a schematic for the process of attaching the protecting group of "BnDppZH" to various amino acids.
Figure 10B:
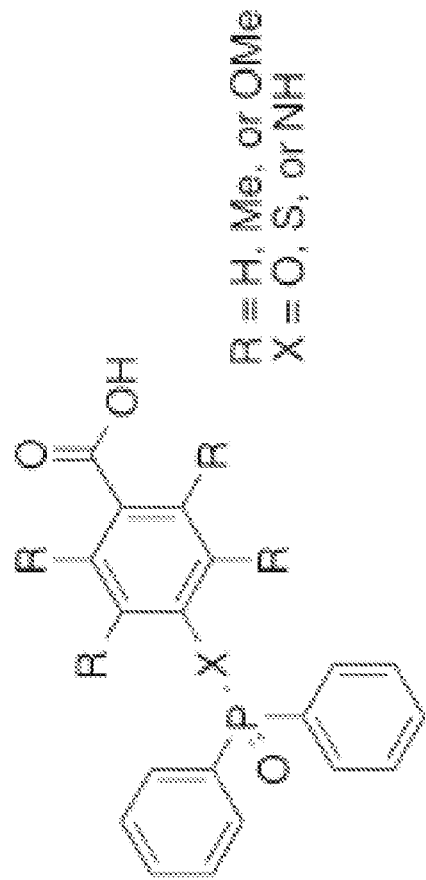
FIG. 10B depicts the protecting group "BzDppOH" utilized in the schematic for the process shown in FIG. 10A.
Figure 10B:
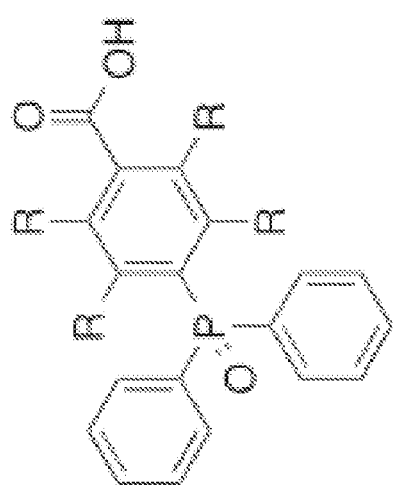

FIGS. 4A-4B each depicts a schematic for the process of attaching the protecting group of FIG. 2 to various amino acids. Other process for attaching protecting groups are shown in FIGS. 9A-9B and 10A-10B. FIG. 9A depicts a schematic for the process of attaching the protecting group of "BnDppYH" to various amino acids. FIG. 9B depicts the protecting group "BnDppYH" utilized in the schematic for the process shown in FIG. 9A. FIG. 10A depicts a schematic for the process of attaching the protecting group of "BzDppOH" to various amino acids. FIG. 10B depicts the protecting group "BzDppOH" utilized in the schematic for the process shown in FIG. 10A.

These additional protecting groups can be used for peptide synthesis in the same fashion as "BnDppOH" consistent with embodiments of the present invention. The peptide coupling reactions for these additional protecting groups can be conducted in ethyl acetate as well as dichloromethane.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among various software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad combinations are possible in achieving the functions, features, and preferences described herein. Moreover, the scope of the present disclosure covers conventionally known manners for carrying out the described features as well as those variations and modifications that may be made to the processes, composition, or compounds described herein as would be understood by those skilled in the art now and hereafter.

Furthermore, the embodiments of methods presented and described as diagrams, schematics or flowcharts in this disclosure (such as the Figures) are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

RELATED REFERENCES

An, G.; Seifert, C.; Li, G. N-Phosphonyl/phosphinyl 1 mmes and group-S assisted purification (GAP) chemistry/technology. Org. Biomol. Chem. 2015, 13, 1600-1617.

Ai, T.; Li, G. Chiral N-phosphonyl imine chemistry: Asymmetric synthesis of a,J3-diamino esters by reacting phosphonyl imines with glycine enolates. Bioorg. Med. Chem. Lett. 2009, 19, 3967-3969.

Han, J.; Ai, T.; Nguyen, T.; Li, G. Chiral N-phosphonyl imine chemistry:asymmetric additions of ester enolates for the synthesis of J3-amino acids. Chem. Biol. Drug Des. 2008, 72, 120-126.

Kattamuri, P. V.; Ai, T.; Pindi, S.; Sun, Y.; Gu, P.; Shi, M.; Li, G. Asymmetric Synthesis of a-Amino-1,3-dithianes via Chiral N-Phosphonyl Imine-Based Umpolung Reaction Without Using Chromatography and Recrystallization. J. Org. Chem. 2011, 76, 2792-2797.

Kattuboina, A.; Kaur, P.; Nguyen, T.; Li, G. Chiral N-phosphonyl imine chemistry: asymmetric 1,2-additions of allylmagnesium bromides. Tetrahedron Lett. 2008, 49, 3722-3724.

Kattuboina, A.; Li, G. Chiral N-phosphonyl imine chemistry: new reagents and their applications for asymmetric reactions. Tetrahedron Lett. 2008, 49, 1573-1577.

Kaur, P.; Wever, W.; Pindi, S.; Milles, R.; Gu, P.; Shi, Ivi.; Li, G. The GAP chemistry for chiral N-phosphonyl imine-based Strecker reaction. Green Chem. 2011, 13, 1288-1292.

Pindi, S.; Kaur, P.; Shakya, G.; Li, G. N-Phosphinyl Imine Chemistry (1): Design and Synthesis of Novel N-Phosphinyl Imines and their Application to Asymmetric aza-Henry Reaction. Chem. Biol. Drug. Des. 2011, 77, 20-29.

Xie, J.-b.; Luo, J.; Winn, T. R.; Cordes, D. B.; Li, G. Group-assisted purification (GAP) chemistry for the synthesis of Velcade via asymmetric borylation of N-phosphinylimines. BeilsteinJ. Org. Chem. 2014, 10, 746-751.

Dailler, D.; Danoun, G.; Baudoin, O. A General and Scalable Synthesis of Aeruginosin Marine Natural Products Based on Two Strategic C(sp(3))-H Activation Reactions. Angell'andte Chemie-International Edition 2015, 54, 4919-4922.

Kaufmann, E.; Hattori, H.; Nliyatake-Ondozabal, H.; Gademann, K. Total Synthesis of the Glycosylated Macrolide Antibiotic Fidaxomicin. Organic Letters 2015, 17, 3514-3517.

Sharma, P. K.; Romanczyk, L. J.; Kondaveti, L.; Reddy, B.; Arumugasamy, J.; Lombardy, R.; Gou, Y.; Schroeter, H. Total Synthesis of Proanthocyanidin AI, A2, and Their Stereoisomers. Organic Letters 2015, 17, 2306-2309.

Wuts, P. G. M. Greene's Protective Groups in Organic Synthesis. 5 ed.; John Wiley & Sons, Inc: New Jersey, 2014.

Isidro-Llobet, A.; Alvarez, M.; Albericio, F. Amino Acid-Protecting Groups. Chem. Rev. 2009, 109, 2455-2504.

Behrendt, R.; Huber, S.; Marti, R.; White, P. New t-butyl based aspartate protecting groups preventing aspartimide formation in Fmoc SPPS. Journal of Peptide Science 2015, 21, 680-687.

Chandrudu, S.; Simerska, P.; Toth, I. Chemical Methods for Peptide and Protein Production. A1olecules 2013, 18, 4373.

Mochizuki, N L; Tsuda, S.; Tanimura, K.; Nishiuchi, Y. Regioselective Formation of Multiple Disulfide Bonds with the Aid of Postsynthetic S-Tritylation. Organic Letters 2015, 17, 2202-2205.

Nlerrifield, R. B. Solid Phase Peptide Synthesis. I. The Synthesis of a Tetrapeptide. J Am. Chem. Soc. 1963, 85, 2149.

Mollica, A.; Pinnen, F.; Azzurra, S.; Costante, R. The Evolution of Peptide Synthesis: From Early Days to Small Molecular Machines. Curr. Bioact. Compd. 2013, 9, 184-202.

Shelton, P. T.; Jensen, K. J. Linkers, Resins, and General Procedures for Solid-Phase Peptide Synthesis. In Peptide Synthesis and Applications, 2nd Edition, Jensen, K. J.; Shelton, P. T.; Pedersen, S. L., Eds. Humana Press Inc: Totowa, 2013; Vol. 1047, pp 323-41.

An, G.; Seifert, C.; Sun, H.; Pan, Y.; Li, G. Group-Assisted Purification (GAP) for Protection of Amino Acids Using N-Phosphonyl Functional Groups. Heterocycles 2015, 90, 344-356.

An, G.; Zhou, W.; Xu, X.; Pan, Y.; Li, G. Solution-Phase-Peptide Synthesis Without Purification of Column Chromatography and Recrystallization by Protecting Amino Acid Esters with Phosphinyl Chloride. Heterocycles 2015, 90, 1405-1418.

Wu, J.; An, G.; Lin, S.; Xie, J.; Zhou, W.; Sun, H.; Pan, Y.; Li, G. Solution-phase-peptide synthesis via the group-assisted purification (GAP) chemistry without using chromatography and recrystallization. Chem. Commun. 2014, 50, 1259-1261.

Brieke, C.; Cryle, 1Vl. J. A Facile Fmoc Solid Phase Synthesis Strategy To Access Epimerization-Prone Biosynthetic Intermediates of Glycopeptide Antibiotics. Organic Letters 2014, 16, 2454-2457.

Chen, C.-C.; Rajagopal, B.; Liu, X. Y.; Chen, K. L.; Tyan, Y.-C.; Lin, F.; Lin, P.-C. A mild removal of Fmoc group using sodium azide. Amino Acids 2014, 46, 367-374.

Spinella, M.; De Marco, R.; Belsito, E. L.; Leggio, A.; Liguori, A. The dimethylsulfoxonium methylide as unique reagent for the simultaneous deprotection of amino and carboxyl function of N-Fmoc-a-amino acid and N-Fmoc-peptide esters. Tetrahedron 2013, 69, 2010-2016.

Amblard, M.; Enomoto, H.; Subra, G.; Fehrentz, J.-A.; Martinez, J. The Fundamentals of Fmoc Solid-Phase Peptide Synthesis. Idenshi Igaku lvfook 2012, 21, 36-42.

Shi, J V L; Yang, Y.; Zhou, X.; Cai, L.; Fang, C.; Wang, C.; Sun, H.; Sun, Y.; Gao, Y.; Gu, J.; Fawcett, J. P. Determination of thymopentin in beagle dog blood by liquid chromatography with tandem mass spectrometry and its application to a preclinical pharmacokinetic study. Journal of Separation Science 2015, 38, 1351-1357.

Zhu, M.-X.; Wan, W.-L.; Li, H.-S.; Wang, J.; Chen, G.-A.; Ke, X.-Y. Thymopentin enhances the generation off-cell lineage derived from human embryonic stem cells in vitro. Experimental Cell Research 2015, 331, 387-398.

Fu, T. T.; Qiao, H. W.; Peng, Z. M.; Hu, G. B.; Wu, X. J.; Gao, Y. X.; Zhao, Y. F. Palladium-catalyzed air-based oxidative coupling of arylboronic acids with H-30 phosphine oxides leading to aryl phosphine oxides. Organic & Biomolecular Chemistry 2014, 12, 2895-2902.

What is claimed is:

1. A method of attaching a protecting group to an amino acid, wherein the method comprises:

reacting a protecting group selected from the group consisting of:

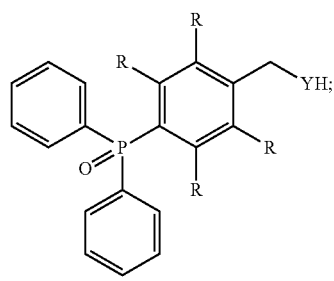
(1B)

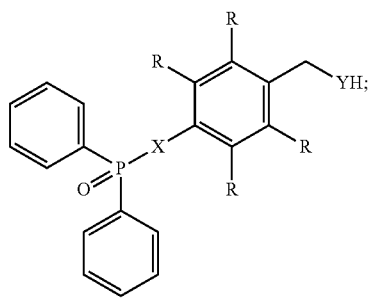
(1C)

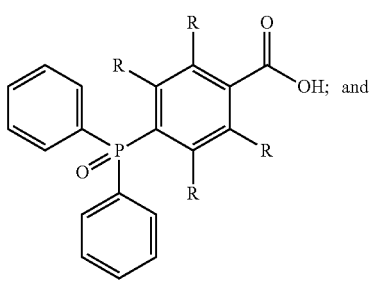
(1D)

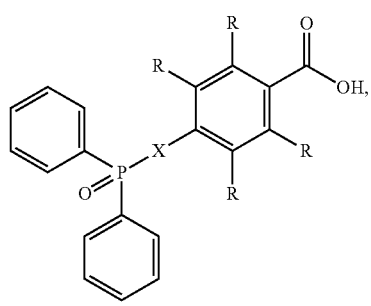
(1E)

wherein:

R is selected from the group consisting of: H, Me, and OMe;

Y is selected from the group consisting of S and NH in 1B, or

Y is selected from the group consisting of: O, S, and NH in 1C, 1D and 1E; and

X is selected from the group consisting of: O, S, and NH with the amino acid to form:

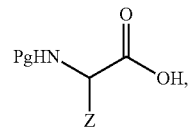

wherein Pg is a protecting group and Z is a general variable.

2. The method of claim 1, wherein the method comprises the steps of:

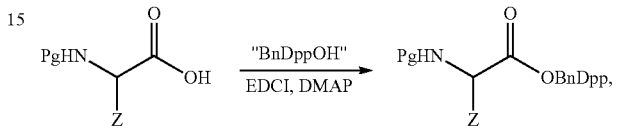

wherein BnDppOH is a protecting group selected from 1C, 1D, or 1E; and wherein Pg is selected from the group consisting of: Cbz, Fmoc, Boc, Bn, Fm, and tBu.

3. The method of claim 1, wherein the method comprises the steps of:

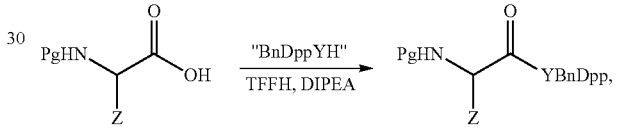

wherein BnDpp YH is a protecting group selected from 1C, 1D, or 1E; and wherein Pg is selected from the group consisting of: Cbz, Fmoc, Boc, Bn, Fm, and tBu.

4. The method of claim 1, wherein the method comprises the steps of:

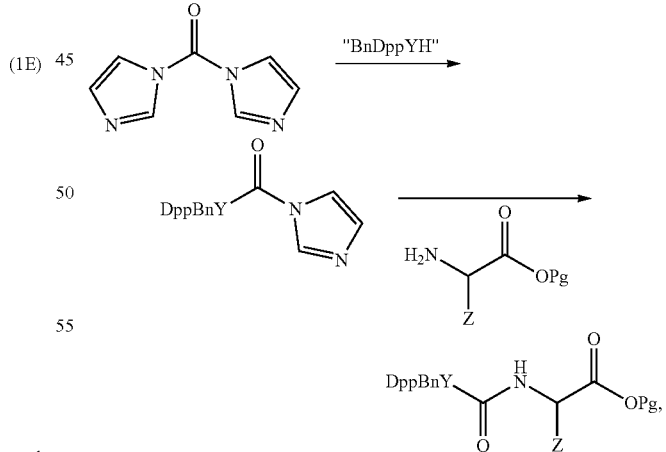

wherein BnDppYH is a protecting group selected from 1C, 1D, or 1E; and wherein Pg is selected from the group consisting of: Cbz, Fmoc, Boc, Bn, Fm, and tBu.

5. The method of claim 1, wherein the method comprises the steps of:

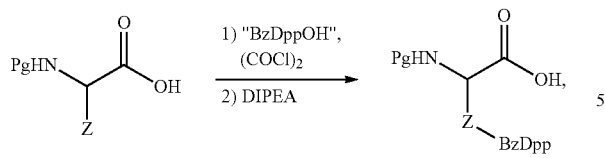

wherein BzDppOH is a protecting group selected from 1C, 1D, or 1E; and wherein Pg is selected from the group consisting of: Cbz, Fmoc, Boc, Bn, Fm, and tBu.

6. The method of claim 5, wherein the protecting group is selected from the group consisting of:

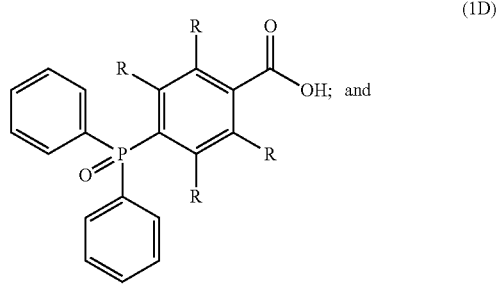

(1D)

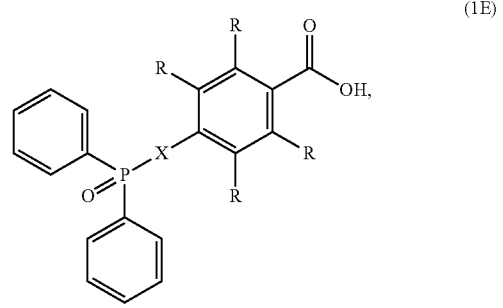

(1E)

wherein R is selected from the group consisting of: H, Me, and OMe; and wherein X is selected from the group consisting of: O, S, and NH.

7. A method of performing a Group Assisted Purification (GAP) peptide synthesis, wherein the method comprises the steps of attaching a protecting group to an amino acid followed by Fmoc-tBu-based solution phase peptide synthesis (SolPPS) coupling reactions on the resulting amino acid having the attached protecting group, wherein the protecting group is selected from the group consisting of:

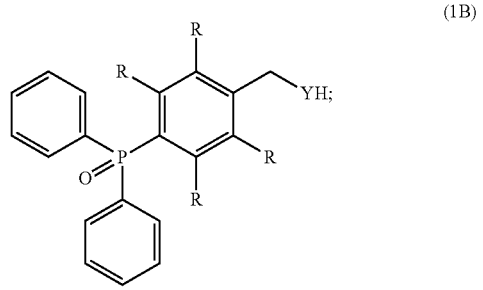

(1B)

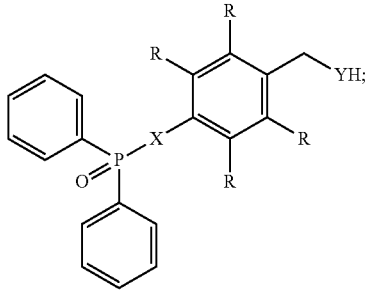

(1C)

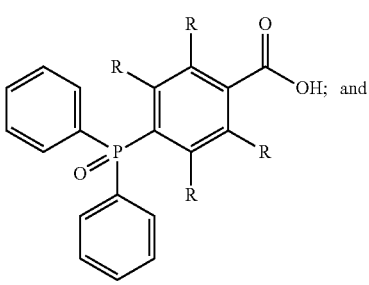

(1D)

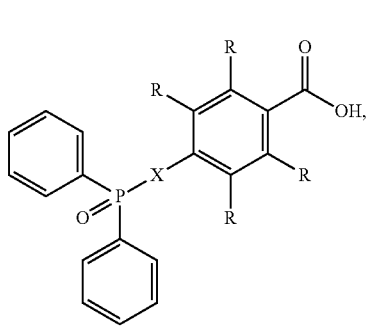

(1E)

wherein:

R is selected from the group consisting of: H, Me, and OMe;

Y is selected from the group consisting of: S and NH for 1B; or

Y is selected from the group consisting of: O, S, and NH for 1C, 1D and 1E, and

X is selected from the group consisting of: O, S, and NH.

8. The method of claim 7, wherein the Fmoc-tBu-based solution phase peptide synthesis (SolPPS) coupling reaction occurs in ethyl acetate.

9. The method of claim 7, wherein the Fmoc-tBu-based solution phase peptide synthesis (SolPPS) coupling reaction occurs in dichloromethane.

* * * * *